US009199052B2

(12) United States Patent
Rubin

(10) Patent No.: US 9,199,052 B2
(45) **Date of Patent: *Dec. 1, 2015**

(54) UNIVERSAL MEDICAL GAS DELIVERY SYSTEM

(71) Applicant: Darren Rubin, Largo, FL (US)

(72) Inventor: Darren Rubin, Largo, FL (US)

( * ) Notice: Subject to any disclaimer, the term of this patent is extended or adjusted under 35 U.S.C. 154(b) by 5 days.

This patent is subject to a terminal disclaimer.

(21) Appl. No.: 14/214,974

(22) Filed: Mar. 16, 2014

(65) Prior Publication Data

US 2014/0200475 A1 Jul. 17, 2014

Related U.S. Application Data

(63) Continuation-in-part of application No. 12/806,032, filed on Aug. 4, 2010, now Pat. No. 8,707,950.

(51) Int. Cl.

| | |
|---|---|
| ***A62B 9/04*** | (2006.01) |
| ***A61M 16/06*** | (2006.01) |
| ***A61B 5/08*** | (2006.01) |
| ***A61M 39/10*** | (2006.01) |
| ***A61M 16/12*** | (2006.01) |
| *A61M 11/06* | (2006.01) |
| *A61M 16/04* | (2006.01) |
| *A61M 16/08* | (2006.01) |

(52) U.S. Cl.

CPC ............ *A61M 16/0605* (2014.02); *A61B 5/082* (2013.01); *A61M 16/06* (2013.01); *A61M 16/085* (2014.02); *A61M 16/0816* (2013.01); *A61M 16/0833* (2014.02); *A61M 16/0875* (2013.01); *A61M 16/125* (2014.02); *A61M 39/1011* (2013.01); *A61M 11/06* (2013.01); *A61M 16/0488* (2013.01); *A61M 16/0666* (2013.01); *A61M 16/0683* (2013.01); *A61M 16/0808* (2013.01); *A61M 39/1055* (2013.01); *A61M 2205/0205* (2013.01); *A61M 2205/0238* (2013.01); *A61M 2205/582* (2013.01); *A61M 2205/583* (2013.01); *A61M 2205/584* (2013.01); *A61M 2206/22* (2013.01); *A61M 2209/08* (2013.01); *A61M 2209/088* (2013.01); *A61M 2230/432* (2013.01)

(58) Field of Classification Search

None

See application file for complete search history.

(56) References Cited

U.S. PATENT DOCUMENTS

| | | | | |
|---|---|---|---|---|
| 5,709,204 | A | 1/1998 | Lester | |
| 2006/0081248 | A1* | 4/2006 | McDonald | 128/205.25 |
| 2006/0196510 | A1* | 9/2006 | McDonald et al. | 128/206.21 |
| 2007/0272245 | A1* | 11/2007 | Ripple et al. | 128/205.28 |
| 2008/0110463 | A1* | 5/2008 | Hajgato et al. | 128/205.25 |
| 2009/0133697 | A1* | 5/2009 | Kwok et al. | 128/205.25 |
| 2009/0320851 | A1* | 12/2009 | Selvarajan et al. | 128/207.13 |
| 2012/0055485 | A1* | 3/2012 | Anthony | 128/207.18 |

* cited by examiner

*Primary Examiner* — Tan-Uyen (Jackie) T Ho
*Assistant Examiner* — Eric Bryant

(57) ABSTRACT

A first source of medical gas has a generally cylindrical male outlet with a cylindrical bore and a threaded outer cylindrical surface. A flexible cylindrical elastomeric medical gas tubing has an input end with a bushing making a flush abutment with the male outlet at the output orifice. An output end attaches to any of a plurality of medical gas utilizing devices, but preferably with a dampening disperser held in position in the space in the vicinity of a patient's nose and mouth. An annular flange of the input end bushing resides within a central cylindrical bored out region extending through the first end and nearly to the second end of a rotatable connector forming an interior surface of a connector with threads coupling with the threads of the male outlet. The second end is an annular abutment against the annular flange holding the input end tubing bushing against the outlet source and providing an airtight coupling. A gripping means is on the exterior surface of the connector.

31 Claims, 19 Drawing Sheets

UNIVERSAL MEDICAL GAS DELIVERY SYSTEM

RELATED APPLICATION

The present application is a continuation-in-part of pending U.S. patent application Ser. No. 12/806,032 filed Aug. 4, 2010, the subject matter of which is incorporated herein by reference.

BACKGROUND OF THE INVENTION

Oxygen is perhaps the most common form of medical gas used by hospitals, clinics, doctor offices, nursing homes, and in homecare. Other types of medical gas include compressed air, oxygen, carbon dioxide, nitrous oxide, nitrogen, helium, and cyclopropane. U.S. Pat. No. 6,581,593 is limited to sources of oxygen gas and oxygen tubing; whereas, the present invention provides a universal medical gas delivery system to be used with all types of medical gas. Furthermore, the present invention also includes numerous other uses and improvements.

Over the years, numerous injuries and deaths have been reported as the result of medical gas mix-ups, which occur when a patient's tubing is connected to the wrong medical gas source and the patient consequently received the wrong type of medical gas. For instance, a patient's oxygen supply tubing may be mistakenly connected to a nitrogen source outlet. Color-coded fittings on both the medical gas tubing and the medical gas source (flow meter) outlet can avoid such errors. Sources and vessels of medical gas may be color-coded as follows: air, yellow; oxygen, green; carbon dioxide, gray; nitrous oxide, blue; nitrogen, black; helium, brown; and cyclopropane, orange. One purpose of this invention is to include color-coded tubing and fittings, such as the rotating nut, corresponding to the type of medical gas prescribed.

However, some caregivers and patients may be color blind. It is another aim of this invention to provide tubing and/or fittings that are labeled for the type of medical gas prescribed. Additionally, the labeling may include raised lettering, indicia, and/or Braille for people with blindness or visual impairment. The tubing and/or connector may also be made from glow-in-the-dark or translucent materials to improve visualization in dark-lit rooms. The tubing may also be illuminated by a light source, such as LEDs, and light may also be transmitted by fiber optic threads incorporated into the tubing, to aid visualization of the tubing system in dark-lit rooms, which provides an advantage over U.S. Pat. No. 7,374,318 and 2010/0020529 that describes a hook apparatus for lighting oxygen tubing.

Medical gas tubing, such as oxygen tubing, that do not come in contact with bodily fluids, are generally disposed of in regular garbage. As a result, each year, millions of units of medical gas supply tubing ends up in both landfills and incineration plants. An additional aim of this invention is to produce medical gas supply tubing from non-toxic materials or polymers that do not release toxins into the air or ground water. A further intention of the current invention is to produce medical gas supply tubing that is more readily degradable in the environment, and may include biodegradable materials and/or additives and/or swelling agents. Said materials may also dissolve with certain solvents. Such design should reduce the environmental impact of disposable tubing supplies.

Oxygen tubing is generally packaged as non-sterile tubing. A further aim of this invention is to manufacture medical gas supply tubing that is composed of radiation resistant materials such that it can be sterilized by radiation, such as by gamma radiation, as disclosed in U.S. Pat. No. 7,622,523. Heat resistant materials may also be employed so that tubing can be autoclaved for sterilization, especially if reused in conjunction with a respiratory machine, such as an anesthesia machine or mechanical ventilator. Furthermore, poor developing nations may need to reuse medical gas tubing supplies as availability of such supplies may be limited. Such sterilization can be important for reducing or preventing cross-contamination in immunocompromised patients. The medical gas tubing and/or connector may also be composed of, or coated with, anti-microbial materials to reduce subsequent contamination, as disclosed in U.S. Pat. No. 7,608,581.

The present invention also reduces contamination and cross-contamination to patient users, since it bypasses the need for supply tubing adapters, many of which are reused between patients stays in the hospital, and become dirty and contaminated when transported in coat pockets and dropped on the floor. With infectious bacteria becoming ever more antibiotic resistance, such as methicillin-resistant *Staphylococcus aureus* (MRSA), any means of limiting patient contamination is desirable. The present invention fulfills this need.

It is a further aim of this invention to prevent patients and/or caregivers from tripping over long medical gas supply tubing. One way to reduce slack is with self-coiling oxygen tubing, comprised of a series of helical coils or loops able to stretch and extend when pulled, and able to retract again when no force is applied, as disclosed in U.S. Pat. No. 4,685,456. If tubing is not self-coiling, then a tubing reel may be used to wind and unwind this tubing to reduce excess tubing length when needed, as disclosed in U.S. Pat. Nos. 5,392,808; 6,591,858; 7,104,491; and 7,487,791 and 2006/0243282.

A swivel element and/or swivel adapter may also be employed to release tension from twisted tubing, as disclosed by U.S. Pat. Nos. 5,284,134; 5,573,280; and 5,797,627. A clip may also be employed to help hold the medical gas tubing onto a patient's clothing, bed, wheelchair, or chair, as disclosed by U.S. Pat. No. 5,188,609.

Medical gas tubing can provide medical gas to a variety of different medical gas utilizing devices. Most often medical gas tubing includes a nasal cannula or a face mask for delivery of gases directly to, or in the vicinity of, the nose and/or mouth. Sometimes the medical gas will dry the patient's airways, and so, a humidifier jar, such as described by U.S. Pat. No. 6,050,552 may be used to humidify the gas. When there is too much humidification, a condensation trap may also be placed in the supply tubing line to capture this excess moisture.

For instance, U.S. Pat. No. 4,106,505 describes a basic nasal cannula held on the head with over-the-ear tubing, while 2004/0035431 describes a nasal cannula with molded ear fittings for a better hold. Nasal cannulas may contain additional sampling tubes for monitoring patient breathing via an electronic detector, such as U.S. Pat. Nos. 7,640,932 and 7,383,839, the latter of which also contains an oral scoop. U.S. Pat. No. 5,575,282 describes an oxygen distributor with both mouth and nose delivery ports and a whirler to provide helical flow of gas.

An alternative to nasal cannulas, which enter the patient's nostrils, are face masks. Face masks come in all shapes and sizes. Some nasal masks only cover the nose, such as U.S. Pat. Nos. 6,651,663; 6,729,333; 6,959,710; D493,523; D502,261; 2002/0148472; 2004/0094158; and 2006/0027236, which describe a triangular nasal mask with headgear attachment.

Other masks are larger and cover both the nose and mouth of the patient. U.S. Pat. No. 7,004,168 and 2003/0047188 describe a face mask for oral and nasal delivery and gas sampling. Face masks can be held in place with elastic straps, or can be held in place with a headgear, which sometimes resembles a phone headset, and often contains arms and joints, which may be adjustable like the mask described by U.S. Pat. No. 7,089,941 and D515,697.

Because masks rest on the face, patients often complain of discomfort. Some have tried to invent masks that are more comfortable. U.S. Pat. No. 6,895,965; 2002,0100479; 20030019496; and 20060076018 describe a face mask with a rotatable elbow, and mask seal with cushion, the seal being formable and customizable to contour the face. Likewise, U.S. Pat. No. 6,698,427 describes a fabric comfort ring for patient medical masks, while 2010/0018535 describes a gel cushion for a mask that forms to the face, and 2005/0051171 describes a nose breathing mask with silicone wax molded for comfort.

For caregiver access to the patient's nose and/or mouth, such as for a patient drinking through a straw or for suctioning of patient fluids, some masks contain one or more access ports or regions, including 2009/0084385; 2003/0024533; and 2008/0110463, the latter of which attaches to a nebulizer to provide aerosol therapy. U.S. Pat. No. 7,255,106 also describes an inhalation mask for use with nebulizer, but unlike 2008/0110463, it does not provide helical flow. Other face masks may contain an exhaust filter, such as described by U.S. Pat. No. 7,503,326. Other masks may be adapted to contain gas supply tubing that extends through the patient's nose and mouth for mechanical ventilation, such as U.S. Pat. No. 6,860,270 describes a face mask for mechanical ventilation that consists of an oral tube and a nasal tube that extends into the intubated patient.

U.S. Pat. Nos. 6,450,166; 6,595,207; 6,631,719; 6,675,796; and 6,837,238; and U.S. Pat. App. Nos. 20040094160; 20050150498; 20060081243; and 20060081248 describe a lightweight oxygen delivery system comprising a baffle to diffuse oxygen which can be delivered to a space in the vicinity of the patient's nose and mouth, when held in position by a boom, or a face mask, but contains a number of cumbersome plastic components, and its tubing, in and of itself, does not have the ability of being securely fastened to a source of oxygen, and so may pop off under high pressure or be pulled off inadvertently, and may also be limited by delivery of only oxygen gas to the patient.

However, many of these medical gas utilizing or delivery devices are still cumbersome, uncomfortable, inconvenient, and potentially unsafe. The present invention, along with its medical gas mask preferred embodiment, provides uncompromised safety and comfort, is easier to manufacture, and can replace many of the existing face masks and cannulas with a single device, to reduce inventory and save hospitals money.

Therefore, it can be appreciated that there exists a continuing need for a new and improved universal medical gas delivery system which can be used for coupling any of a plurality of different medical gas sources to a medical gas tube leading to any of a plurality of different medical gas utilizing devices. In this regard, the present invention substantially fulfills this need.

SUMMARY OF THE INVENTION

In view of the foregoing disadvantages inherent in the known types of medical gas delivery systems of known designs and configurations now present in the prior art, the present invention provides an improved universal medical gas delivery system. As such, the general purpose of the present invention, which will be described subsequently in greater detail, is to provide a new and improved universal medical gas delivery system and method which has all the advantages of the prior art and none of the disadvantages.

To attain this, the present invention essentially comprises a universal medical gas delivery system for coupling any of a plurality of different medical gas sources to a medical gas tube leading to any of a plurality of different medical gas utilizing devices. First provided is a first source of medical gas. The first source comprises a generally cylindrical male outlet. The male outlet has an output orifice and an inner bore through which source medical gas is adapted to pass. The male outlet also has an outer cylindrical surface with threads.

Next provided is a flexible cylindrical elastomeric medical gas tubing. The gas tubing is of an extended length and has an inner diameter and outer diameter. The gas tubing also has a first input end and a remote second output end. The first input end further comprises a bushing that makes a flush abutment with the first outlet source of medical gas at the output orifice. The second output end is adapted to attach to any of a plurality of medical gas utilizing devices. An annular flange of the first input end bushing is adapted to reside within a bored out region of a connector thereby preventing the tubing/bushing from being separated from the connector.

The connector is rotatable and has a first opening at a first end and a second opening at a second end. The bored out region of the connector is central and generally cylindrical and extends through the first end and nearly to the second end forming an interior surface. The interior surface of the connector has threads and is adapted to couple with the threads of the male outlet source of medical gas. The second end opening of the connector has a diameter less than the diameter of the annular flange of the first input end tubing bushing. The second end of the connector serves as an annular abutment against the annular flange thereby holding the first input end tubing bushing against the first outlet source of medical gas when the connector is screwed on and also provides an airtight coupling.

Next provided is at least one user gripping means on the exterior surface of the connector. The gripping means assists a user in the coupling/screwing of the connector to the outlet source of medical gas. The gripping means is chosen from physical gripping means including, but not limited to, grooves, fingertip indentations, radially protruding flanges, angled surfaces and edges, curved surfaces and edges, surface bumps and friction-causing rough surfaces.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims attached.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved universal medical gas delivery system which has all of the advantages of the prior art medical gas delivery systems of known designs and configurations and none of the disadvantages.

It is another object of the present invention to provide a new and improved universal medical gas delivery system which may be easily and efficiently manufactured and marketed.

It is further object of the present invention to provide a new and improved universal medical gas delivery system which is of durable and reliable constructions.

An even further object of the present invention is to provide a new and improved universal medical gas delivery system which is susceptible of a low cost of manufacture with regard to both materials and labor, and which accordingly is then susceptible of low prices of sale to the consuming public, thereby making such universal medical gas delivery system economically available to the buying public.

Even still another object of the present invention is to provide a universal medical gas delivery system for coupling any of a plurality of different medical gas sources to a medical gas tube leading to any of a plurality of different medical gas utilizing devices.

Lastly, it is an object of the present invention to provide a new and improved universal medical gas delivery system. A first source of medical gas has a generally cylindrical male outlet with a cylindrical bore and a threaded outer cylindrical surface. A flexible cylindrical elastomeric medical gas tubing has an input end with a bushing making a flush abutment with the male outlet at the output orifice. An output end attaches to any of a plurality of medical gas utilizing devices. An annular flange of the input end bushing resides within a central cylindrical bored out region extending through the first end and nearly to the second end of a rotatable connector forming an interior surface of a connector with threads coupling with the threads of the male outlet. The second end is an annular abutment against the annular flange holding the input end tubing bushing against the outlet source and providing an airtight coupling. A gripping means is on the exterior surface of the connector.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

The same reference numerals refer to the same parts throughout the various Figures.

DESCRIPTION OF THE PREFERRED EMBODIMENT

Figure 1:
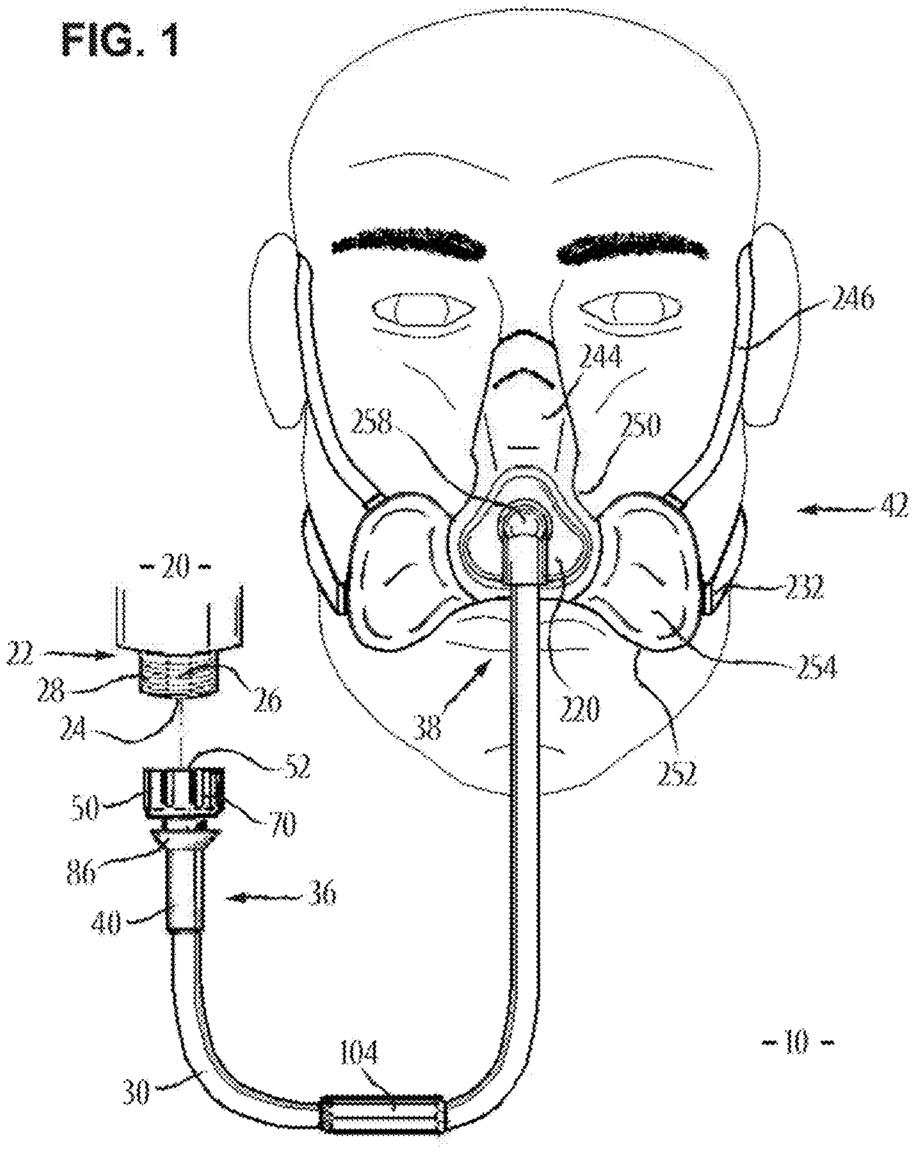
FIG. 1 is an improved universal medical gas delivery system consisting of medical gas tubing with rotatable threaded connector and tubing bushing, at first input end, that attaches to a source of medical gas (flow meter outlet), and is able to transfer medical gas to a respiratory gas utilizing device, at remote second output end, and in this figure, is shown with the third preferred embodiment of a dampening disperser in partial face mask housing, along with swivel elements.

With reference now to the drawings, and in particular to FIG. 1 thereof, the preferred embodiment of the new and improved universal medical gas delivery system embodying the principles and concepts of the present invention and generally designated by the reference numeral 10 will be described.

The present invention, the universal medical gas delivery system 10 is comprised of a plurality of components. Such components in their broadest context include a source of medical gas, a flexible cylindrical elastomeric medical gas tubing, a connector and a gripping means. Such components are individually configured and correlated with respect to each other so as to attain the desired objective.

The universal medical gas delivery system 10 is for coupling any of a plurality of different medical gas sources to a medical gas tube leading to any of a plurality of different medical gas utilizing devices. First provided is a first source of medical gas 20. The first source comprises a generally cylindrical male outlet 22. The male outlet has an output orifice 24 and an inner bore 26 through which source medical gas is adapted to pass. The male outlet also has an outer cylindrical surface with threads 28.

Figure 2:
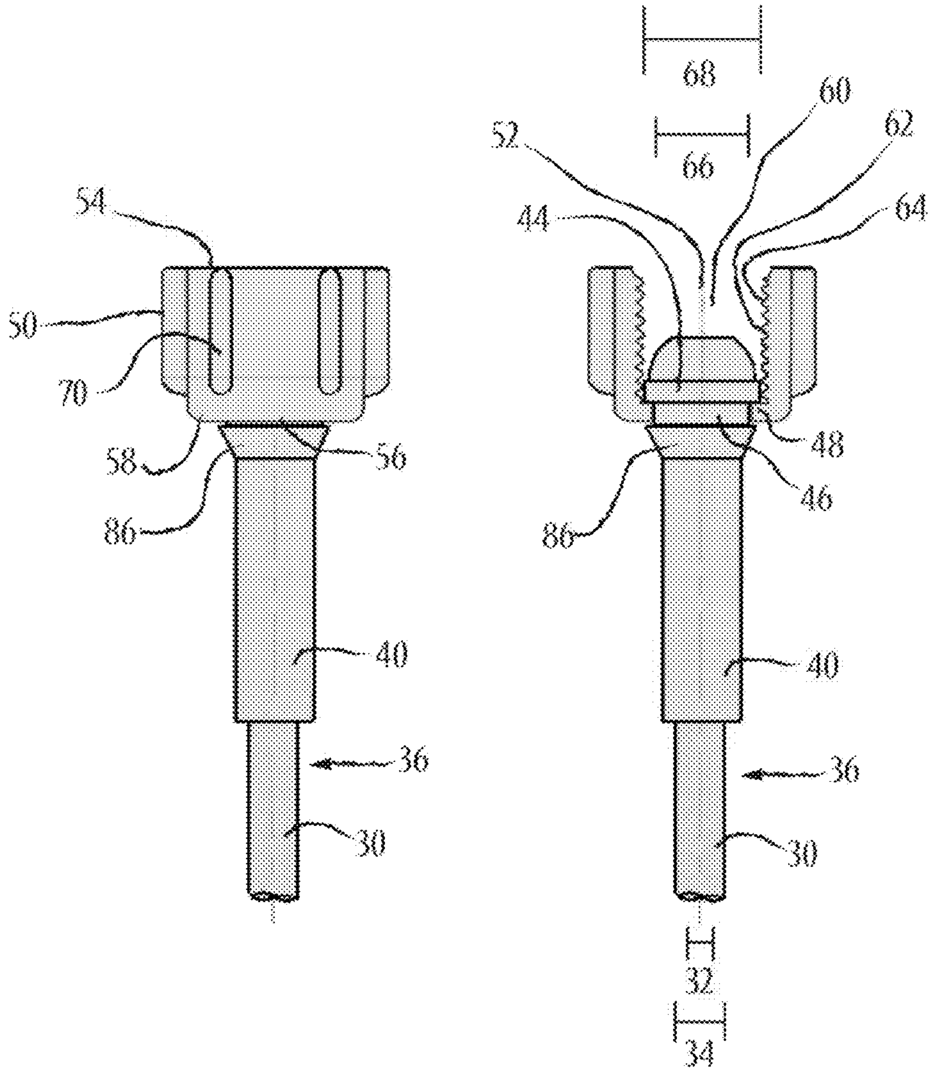
FIG. 2 is the first preferred embodiment of the threaded rotatable connector, with gripping means, and the medical gas tubing bushing, with annular flange and sliding-preventing (distance limiting) means; shown intact (left) and cross-section (right).
Figure 3:
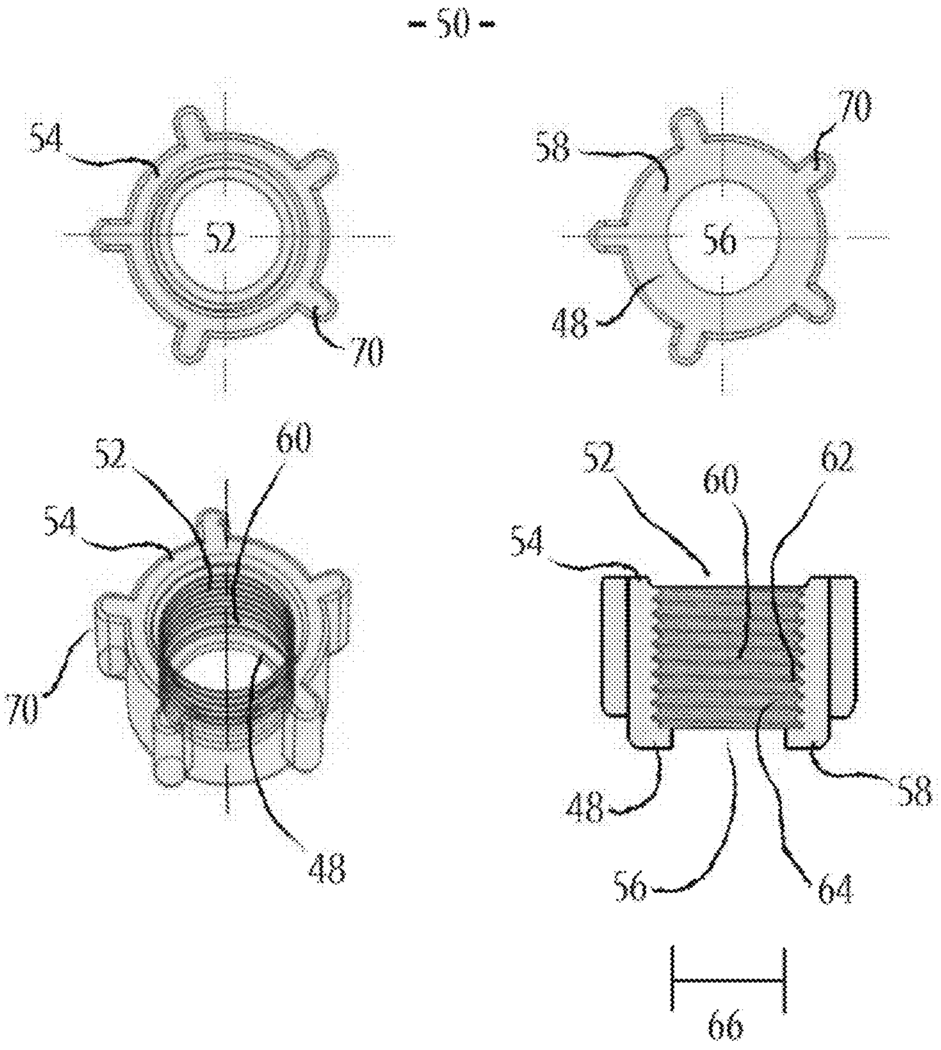
FIG. 3 provides greater detail of the threaded rotatable connector of the first preferred embodiment, viewed from the top down (top left of figure), bottom up (top right of figure), transparent three-dimensional view (bottom left of figure), and cross-section (bottom right of figure).

Next provided is a flexible cylindrical elastomeric medical gas tubing 30. The gas tubing is of an extended length and has an inner diameter 32 and outer diameter 34. The gas tubing also has a first input end 36 and a remote second output end 38. The first input end further comprises a tubing bushing 40 that makes a flush abutment with the cylindrical male outlet 22 of the source of medical gas at the output orifice 24. The remote second output end 38 is adapted to attach to any of a plurality of medical gas utilizing devices 42. In FIGS. 2 and 3, an annular flange 44 of the first input end tubing bushing 40 is adapted to reside within a bored out region 60 of a rotatable connector 50 thereby preventing the flexible cylindrical elastomeric medical gas tubing (30) and input end tubing bushing (40) from being separated from the connector.

The connector 50 is rotatable and has a first opening 52 at a first end 54 and a second opening 56 at a second end 58. The bored out region 60 of the connector is central and generally cylindrical 60 and extends through the first end 54 and nearly to the second end 58 forming an interior surface 62. The interior surface of the rotatable connector has threads 64 and is adapted to couple with the threads 28 of the cylindrical male outlet 22 of the source of medical gas 20. The second end opening 56 of the rotatable connector has a diameter 66 less than the diameter 68 of the annular flange 44 of the first input end 36 tubing bushing 40. The second end 58 of the connector serves as an annular abutment 48 against the annular flange 44 thereby holding the first input end tubing bushing 40 against the first outlet 22 source of medical gas when the connector 50 is screwed on and also provides an airtight coupling.

Next provided is at least one user gripping means 70 on the exterior surface of the connector. The gripping means assists a user in the coupling/screwing of the connector 50 to the outlet 22 source of medical gas 20. The gripping means 70 is chosen from physical gripping means including, but not limited to, grooves, fingertip indentations, radially protruding flanges, angled surfaces and edges, curved surfaces and edges, surface bumps and friction-causing rough surfaces.

At least one component of the first input end tubing bushing 40 is comprised of material chosen from a class of materials including, but not limited to, rigid materials, semi-rigid materials, semi-flexible materials, flexible materials and combinations of such materials thereof. Such materials include, but are not limited to, hard plastic, soft plastic, polymers, composites, polyethylene, polyvinyl chloride/PVC, acrylonitrile butadiene styrene/ABS, latex, silicone, metal and combinations thereof.

At least one component of the rotatable connector 50 is comprised of material chosen from a class of materials including, but not limited to, rigid materials, semi-rigid materials, semi-flexible materials, flexible materials and combinations of such materials thereof. Such materials include, but are not limited to, hard plastic, soft plastic, polymers, composites, polyethylene, polyvinyl chloride PVC, acrylonitrile butadiene styrene/ABS, latex, silicone, metal and combinations thereof.

In preferred embodiments of the invention, the connector 50 spins independently of the medical gas tubing 30 and screws onto the medical gas threaded male fitting 22 while the medical gas tubing 30 remains stationary. In this manner unnecessary twisting of the tubing is prevented.

In preferred embodiments of the invention, the medical gas tubing 30 cannot be disconnected from the medical gas threaded male fitting 22 once the threaded female connector 50 has been securely screwed onto this fitting. In this manner, the medical gas tubing 30 cannot be inadvertently pulled off and cannot be blown off as a result of gas pressure once the connector is coupled to this medical gas threaded male fitting 22.

Figure 4:
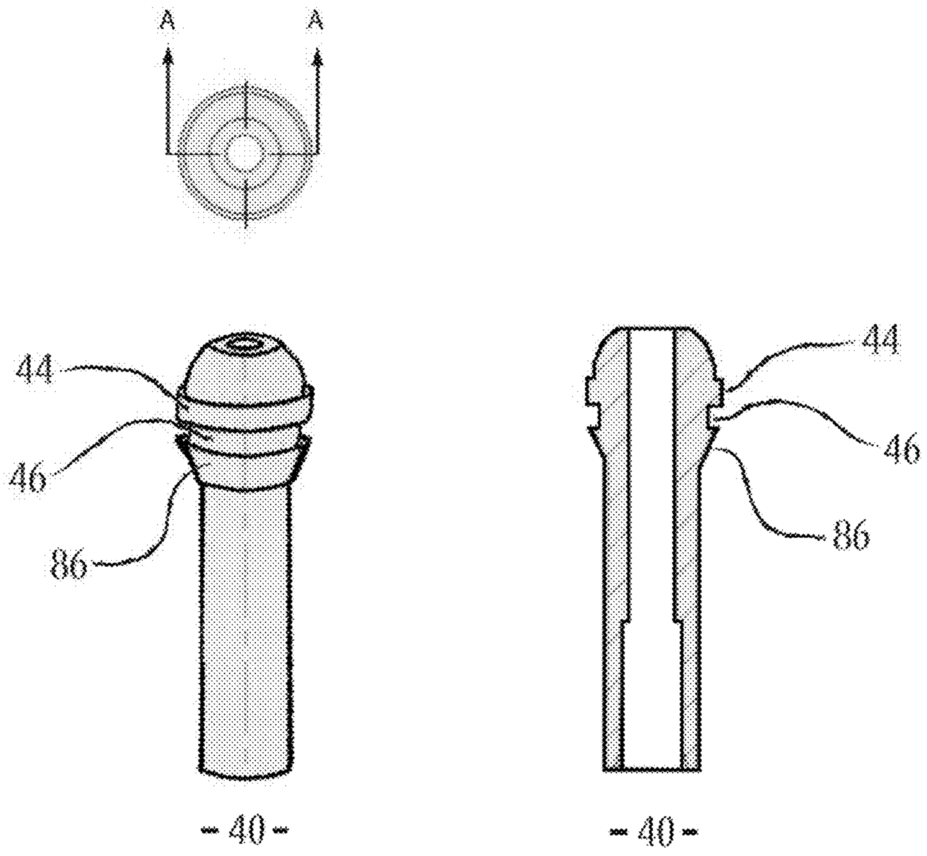
FIG. 4 provides greater detail of the medical gas tubing bushing in three-dimensions and cross-section, and also reveals the annular groove/track that the second end of the rotatable connector sits into to prevent the connector from sliding along the tubing.

In another preferred embodiment FIG. 4, the tubing end/bushing 40 further comprises an annular groove/indentation/track 46 adapted to house/contain at least some of the second end 58 walls/structure, the annular abutment 48 of the rotatable connector 50. The grooved track 46 allows the rotatable connector 50 to spin but prevents the rotatable connector from sliding along the axis 84 of the tubing to any appreciable extent. The grooved track 46 serves the purpose of the annular flange provided in other embodiments to prevent the connection from leaking gas and from the connector coming off the bushing. The tubing end bushing 40 has a general shape selected from the type of general shapes including, but not limited to, a cylindrical shape, curved shape, ball shape, semi-spherical shape, triangular shape, rectangular shape, trapezoid shape, bowl shape and any combination shape thereof.

Figure 5:
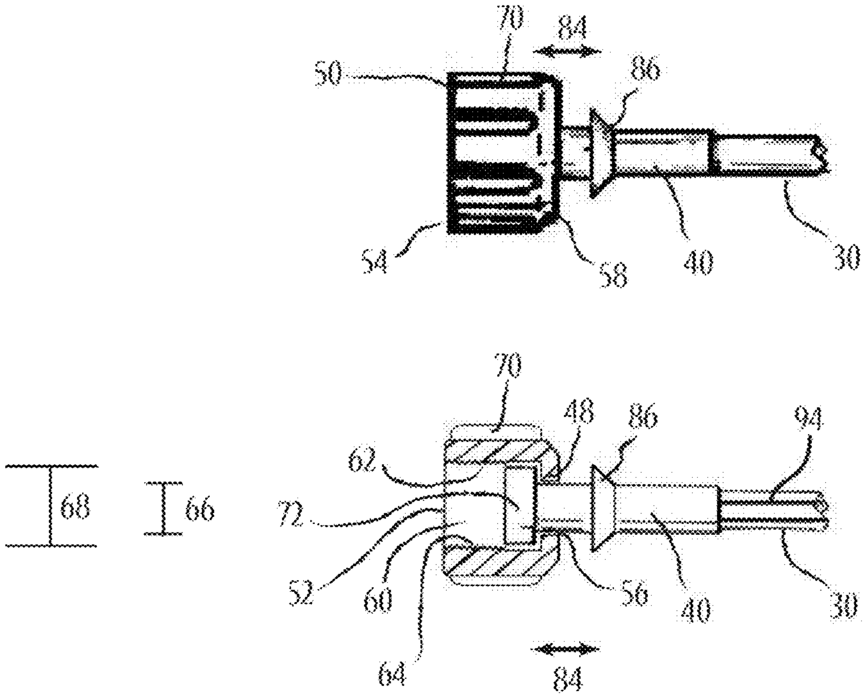
FIG. 5 is another first preferred embodiment of the threaded rotatable connector, with gripping means, and the medical gas tubing bushing; shown intact (top) and cross-section (bottom). In this embodiment, an elastomeric seal is provided at the bushing tip, and the connector is able to slide a limited distance to expose some of the bushing. The tubing is lumen tubing that contains reinforced, parallel channels to prevent tubing from kinking.

In another preferred embodiment of the invention FIG. 5, at least one seal 72 is provided to prevent gas leakage between the tubing connector 50 and the medical gas threaded male fitting outlet or inlet 22. The seal 72 is a fluidic mechanical seal selected from a class of mechanical seals including, but not limited to, washers, O-rings, X-rings, Q-rings, square rings and gaskets and further selected from mechanical seals that are removably placed within the medical gas delivery system and mechanical seals that are an integral component of the medical gas delivery system and any combinations thereof.

Figure 8:
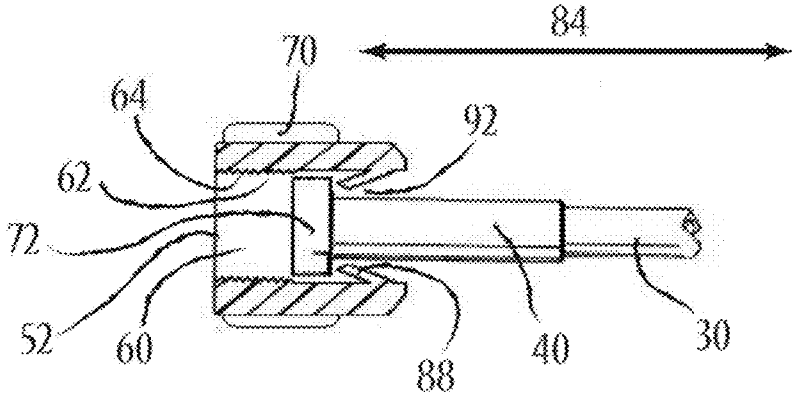
FIG. 8 is another first preferred embodiment of the threaded rotatable connector, with gripping means, and the medical gas tubing bushing shown cross-section (top). The second end of the rotatable connector has an annular recess, comprised of four flanges (bottom), which allows the connector to be pushed onto the bushing during manufacture, but cannot be taken off. There are no means of preventing the connector from sliding along the tubing, but these four flanges may catch on the tubing and reduce sliding by friction. The bushing can be fully exposed in this embodiment. An elastomeric washer comprises the annular flange of the tubing bushing.
Figure 8:
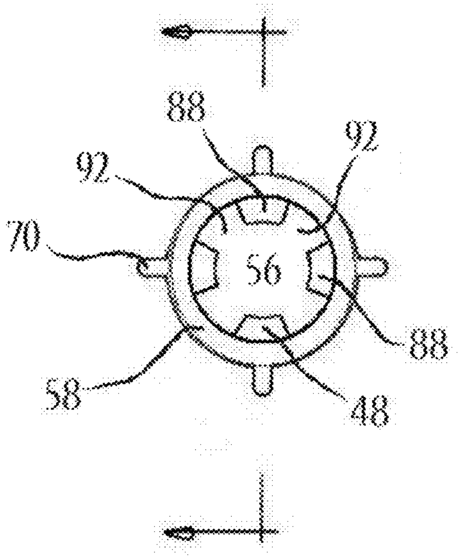

In yet another preferred embodiment of the invention FIG. 8, the medical gas tubing 30 has an end that includes at least one elastomeric washer 72 to aid in providing an airtight seal between the connector 50 and the medical gas threaded male fitting 22. The elastomeric washer 72 can be integrally included as part of, in addition to, or instead of the annular flange 44.

Figure 6:
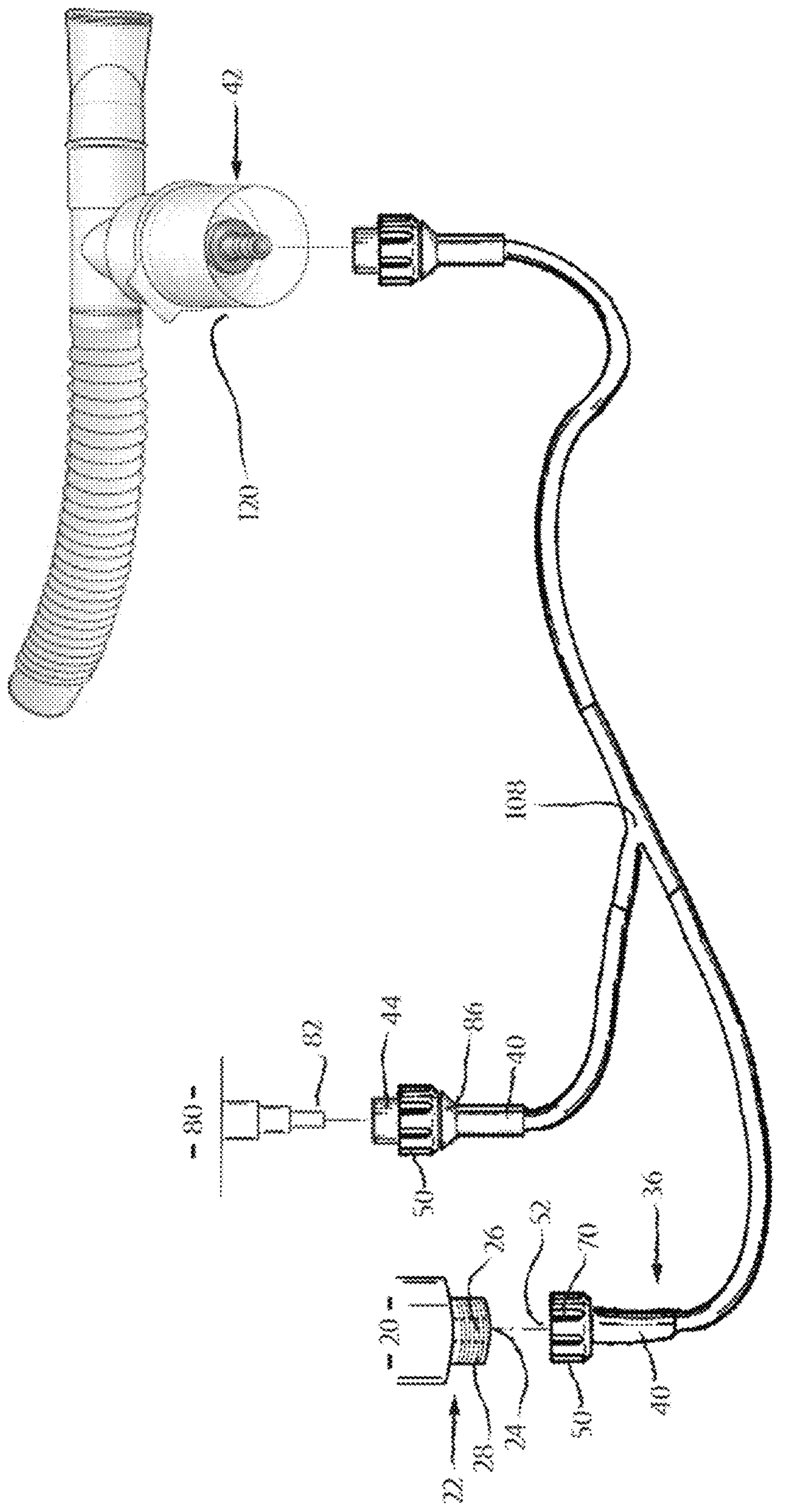
FIG. 6 is a second preferred embodiment of tubing containing a Y-junction allowing for two input terminals, each able to connect to a different source of medical gas, which may be important for administering anesthesia. The first outlet is a threaded, cylindrical male outlet allowing the connector to screw on; while the second outlet is a barbed stem (or nipple) that the tubing bushing can push onto. The rotatable and slidable connector is also found on the output terminal of the tubing, allowing it to connect to a respiratory gas utilizing device, such as a nebulizer (as shown).

In another preferred embodiment of the invention FIG. 6, the universal medical gas delivery system has a second/alternate source of medical gas 80. The second source of medical gas has an output end 82, nipple, nipple and nut adapter, barbed outlet, tubular outlet, of a reduced diameter with an axial inner bore through which source medical gas is adapted to pass. The reduced output end 82 is adapted to couple within the first input end 36 of the medical gas tubing/bushing 40 and allow the medical gas to pass from the source 80 to the tubing 30. The rotatable connector 50 is adapted to be used to help the user grip and push/pull on the tubing end to force the tubing first input end bushing 40 onto and over the nipple outlet 82 more tightly.

In still another preferred embodiment FIG. 5, the rotatable connector 50 can be slid up and down, back and forth, along the axis 84 of the tubing 30. In this manner it is slid away to expose the tubing end bushing 40 during coupling of the tubing end with a rigid tubular "nipple" structure, such as the nipple of a second source of medical gas outlet 82 or the nipple of a respiratory device 42. In this embodiment, means 86 can be provided for limiting the distance that the rotatable connector can travel from the tubing end, so as to not travel too far. The means for limiting this sliding distance of the rotatable connector 50 along the tubing can be chosen from such distance limiting means including, but not limited to, a barrier, such as an annular flange, washer, O-ring, dimple, bump, clasp, groove and wedge, on or as part of the tubing and/or bushing and friction causing means including, but not limited to, rough surfaces, jagged or disjointed edges and alternate embodiment flanges 88 of the annular recess of the second end 58 of the rotatable connector 50 that catches the tubing 30.

In another preferred embodiment FIG. 2, the rotatable connector 50 cannot be slid up and down back and forth along the axis of the tubing. The means 86 provided for preventing the rotatable connector from sliding along the axis 84 of the tubing can be chosen from such distance limiting means including, but not limited to, at least one barrier, such as an annular flange, washer, O-ring, dimple, bump, clasp and wedge, on or as part of the tubing and/or first end bushing. Said barrier 86 is unable to pass through the opening 56 of the second end 58 of the rotatable connector 50.

Figure 7:
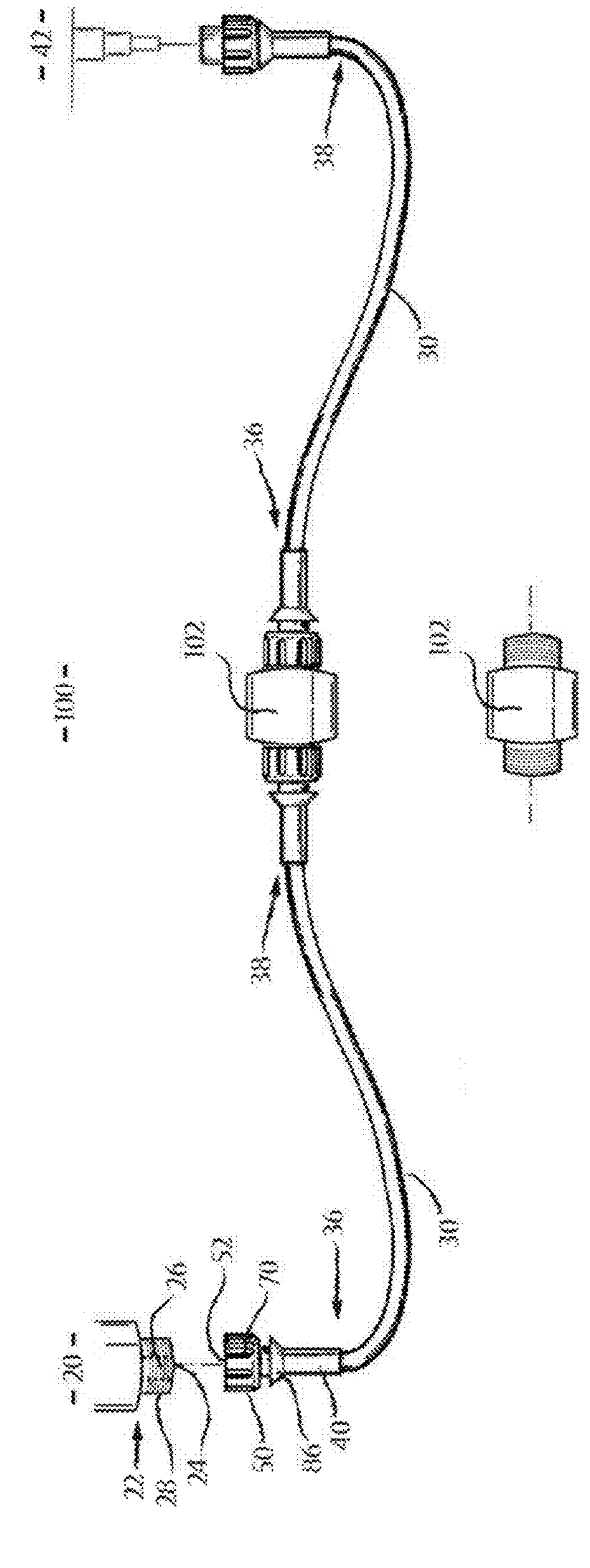
FIG. 7 is a second preferred embodiment with rotatable connectors on both ends of the tubing, thereby, allowing tubing to be connected in series using an adapter interface, such as to extend tubing length between the first source of medical gas and the respiratory gas utilizing device.

In other preferred embodiments FIGS. 6 and 7, the medical gas tubing 30 has at least one input terminal and at least one output terminal and at least one rotatable connector on the at least one input terminal and at least one output terminal.

In still other preferred embodiments FIGS. 6 and 7, the system is adapted to connect to at least one of a plurality of medical gas utilizing devices 42, including medical gas utilizing devices having a generally cylindrical male inlet with an input orifice and an inner bore through which medical gas is adapted to pass and an outer cylindrical surface having threads able to couple with the threads of the female rotatable connector of the medical tubing output end/terminal as the connector is screwed on; and medical gas utilizing devices with a tubular "nipple" inlet of a reduced diameter with an axial bore which medical gas is adapted to pass, that an output end/terminal of the medical gas tubing can be pushed onto/over.

In another preferred embodiment FIG. 8, the rotatable connector 50 has an annular recess 92 of its second end 58 comprised of at least one flange 88 which allows the connector 50 to be pushed over the annular flange 44 of the tubing first end/bushing 40 during manufacture and assembly. The connector 50, however, cannot be pushed back over the annular flange 44 in the opposite direction. In addition, the at least one flange 88 of the connector can be angled non-perpendicular to the tubing and semi-flexible/bendable to achieve this association with the tubing.

The tubing provided is crush-resistant and kink-resistant as shown in FIG. 5. This type of tubing is otherwise known as "lumen tubing". This tubing contains one or more channels 94 along or within the tubing walls for reinforcing the tubing.

In second preferred embodiments FIG. 7, illustrated by the system identified by reference numeral 100, the universal medical gas delivery system is a plurality of systems are connected in series 100. These second preferred embodiments are for extending tubing length. These embodiments use an adapter 102 chosen from adaptors including, but not limited to, an adapter with at least two threaded male plugs that tubing threaded female connectors can screw onto, an adaptor with at least two nipples that tubing can push onto, and an adaptor with at least one threaded male plug and at least one nipple.

At least one swivel element/swivel adaptor 104 is provided FIG. 1 to release tension from twisted tubing as the element can be rotated. The swivel element can be chosen from a class of swivel elements including, but not limited to, ball joints, hollow cylindrical rod-like housings that contain another rod-like structure of smaller diameter inside of it and allowed to rotate within it and cylindrical rod-like structures able to turn freely within a support structure along with means are of preventing said swivel element from dissociating, chosen from such means including, but not limited to nuts, washers, pins and flanges.

Figure 9:
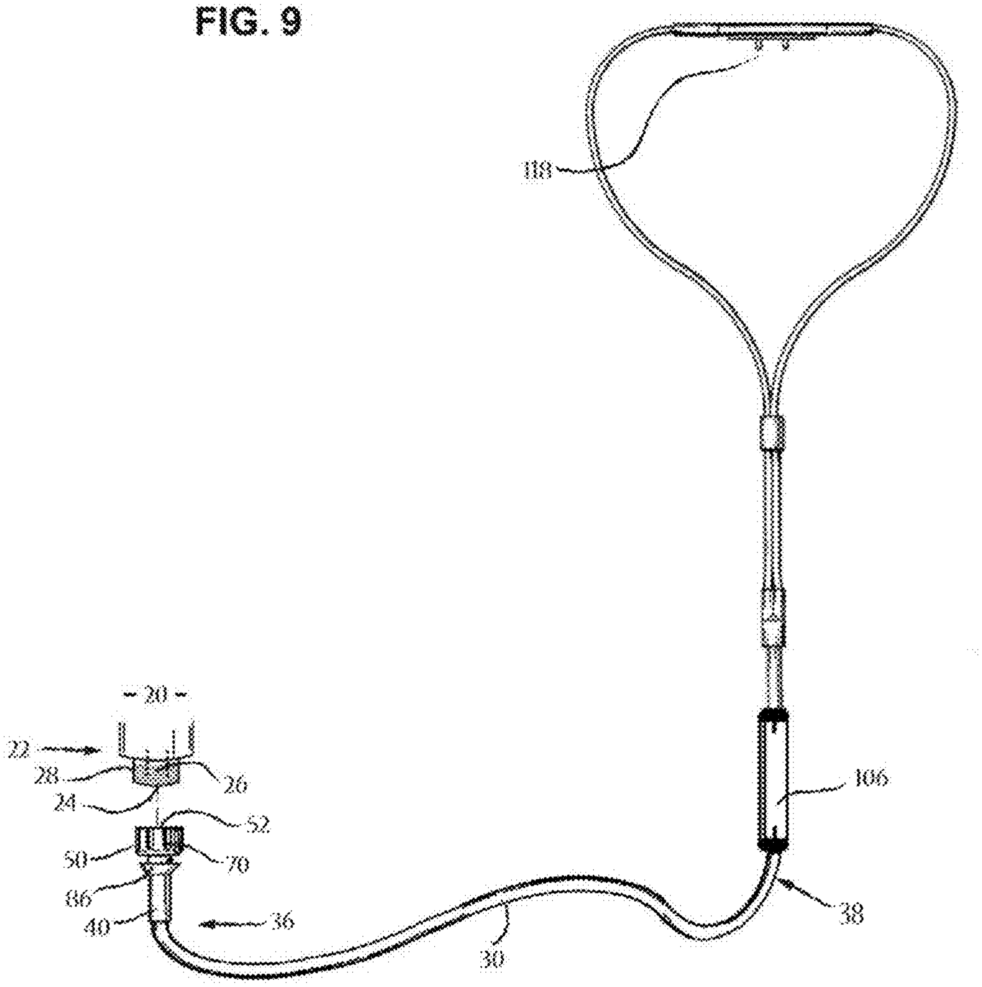
FIG. 9 is another second preferred embodiment that includes a condensation/water trap and a nasal cannula as a respiratory gas utilizing device.

In FIG. 9, further provided is a condensation trap tubing such as a water trap 106. Such trap functions to entrain moisture and humidity in the tubing.

Next an adapter/junction FIG. 6, such as an "X" and "Y" adapter and junction 108 is provided for connection to multiple sources of medical gas and to multiple respiratory devices/gas utilizing devices.

A quick disconnect element is next provided.

In second preferred embodiments, the medical gas supply tubing that is provided is self-coiling and comprised of a series of helical coils, loops able to stretch and extend when pulled and able to retract again on its own, when not pulled.

In second preferred embodiments, a tubing reel is provided to wind and unwind tubing to reduce excess tubing length as needed. This tubing reel may be manual and self-retracting.

In second preferred embodiments, a clip or swivel clip is provided. The clip functions to hold the gas tubing onto a patient's clothing, bed, wheelchair, or chair.

Figure 10:
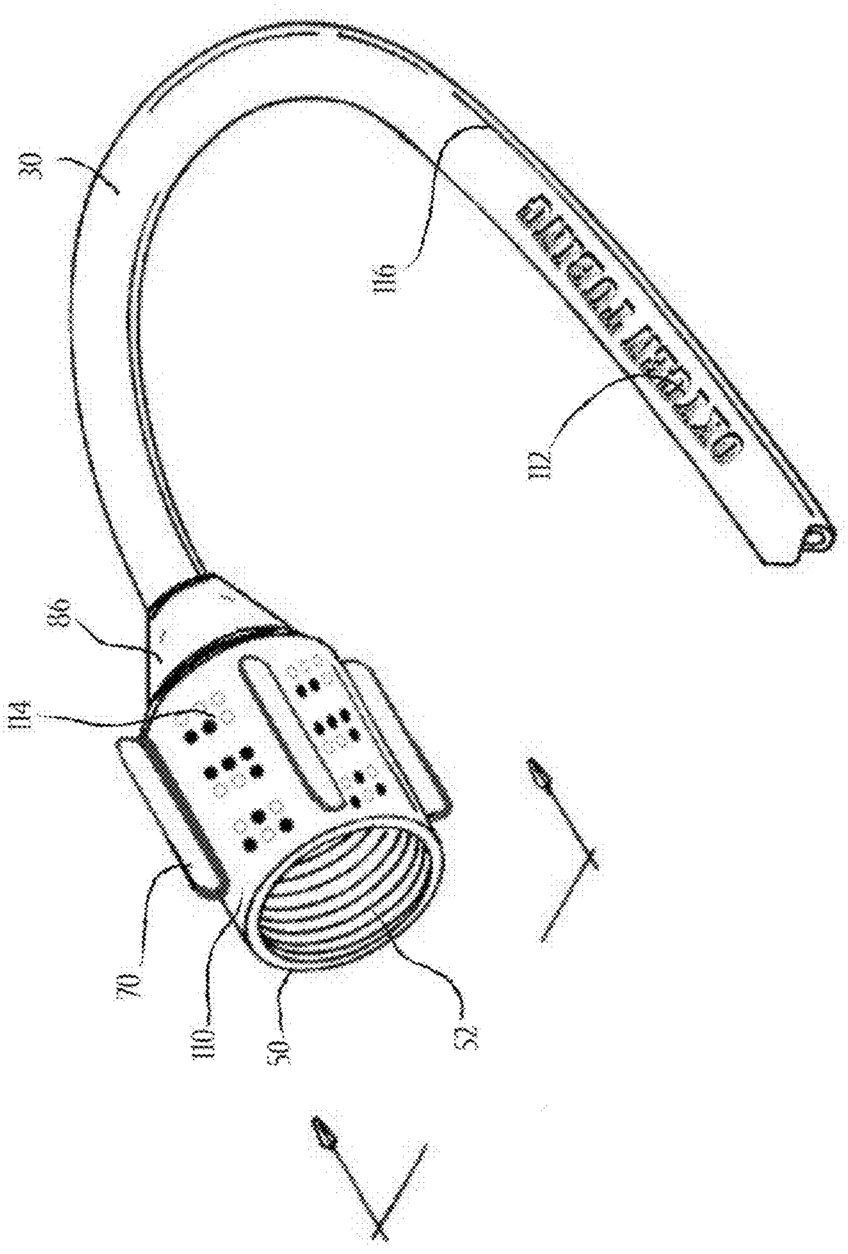
FIG. 10 is another second preferred embodiment that helps patients and health care workers utilize the correct gas source. The rotatable connector is color-coded, and includes raised Braille lettering to indicate which type of gas source to be used with this system. The tubing also includes glow-in-the-dark indicia that spells out the correct gas type. Also shown are fiber optic threads that provide tubing visibility at night, to prevent caregivers from tripping on the tubing.

Further, in second preferred embodiments, shown in FIG. 10, at least one component 110 that is color coded is provided for safety. The color coded component helps direct the user or care giver to the proper source of medical gas to avoid errors. Alternatively, at least one component is labeled to indicate the type of medical gas to be used. Labeling may be used for people with visual impairment including color blindness. The labeling can include raised lettering 112, indicia and/or Braille 114 to indicate the type of medical gas to be used. Also, alternatively, at least one component may be made from a glow-in-the-dark and/or translucent material, such as to aid visualization of the tubing system in dark-lit rooms. The tubing may be illuminated by a light source, such as LEDs and fiber optic threads 116 incorporated into the tubing.

In second preferred embodiments, the medical gas supply tubing and connector are comprised of and/or coated with anti-microbial materials to reduce microbial growth and contamination.

The at least one gas source is chosen from medical gas sources selected from a class of respiratory gas sources including, but not limited to, gas tanks, air compressors, oxygen concentrating devices, oxygen concentrators and wall-mounted flow meters; and capable of delivering medical gas chosen from the types of medical gases selected from a class of inhalable medical gases including, but not limited to, compressed air, oxygen, carbon dioxide, nitrous oxide, nitrogen, helium, carbon monoxide, nitric oxide, hydrogen sulfide, cyclopropane, other anesthesia gases and any combinations thereof.

The at least one respiratory apparatus is chosen from medical gas utilizing apparatuses selected from a class of respiratory gas utilizing devices including, but not limited to, nasal cannulas 118 (FIG. 9), face masks, venturi valves, venturi masks, mouthpieces, endotracheal catheters/endotracheal adapters, nebulizers/atomizers 120 (FIG. 6), aerosol masks, vaporizers, inhalers, aerosol holding chambers/spacers, spirometers, humidifier jars, humidifier devices, positive airway pressure devices, positive expiratory pressure devices, resuscitation bags also called artificial resuscitator, reanimation/resuscitation bag, "Ambu bag", gas mixing devices gas mixers, flow regulators, flow sensors, hyperbaric oxygen chambers, incubators, mechanical ventilators, ventilator line oxygen port adaptors, anesthesia machines/anesthesia ventilators, other respiratory line adapters and fittings and any combinations thereof.

Third preferred embodiments of the present universal medical gas delivery system invention (FIGS. 1, and 11 through 19) are comprised of a dampening disperser that reduces the velocity of medical gas flowing from the source of medical gas to a space in the vicinity of the patient's nose and mouth, such as between the upper lip and the base of the nose, while generating vortices to mix the gases in the vicinity of the patient's nose and mouth. This allows for both nose breathing and mouth breathing of these gases. The dampening disperser releases medical gas in a way that causes at least some turbulence and negative interference to slow the velocities of the gas streams, to reduce full impact of gas flow with the patient's face. The interference can also cause angular momentum and circular motion to further enhance vortex formation and gas mixing. Vortex formation and gas mixing are important for clearing exhaled breath away from the patient and can also allow for mixing of medical gas with ambient air in approximately this same space. The interior walls of the dampening disperser, which contain at least one gas outlet nozzle that dispenses gas within/into the interior region of the dampening disperser, are concave cup-like in shape, and these walls can be angled to help focus and direct gas vortices toward the patient, such as towards the patient's mouth. The dampening disperser can be attached to a variety of different supports in communication with the patient's head to position the dampening disperser in the vicinity of the patient's nose and mouth. Different supports include that of an at least a partial face mask housing of full or partial face masks. Gas outlets of the dampening disperser can meet at a junction. The dampening disperser is connected to at least one medical gas tube. The medical gas tubing can be connected to the flow meter of at least one medical gas source, utilizing the rotatable rigid connector described herein. The rotatable rigid connector described herein can provide a safe and reliable connection to the medical gas source, that cannot be inadvertently pulled off, or shot off by pressure, such as when the flow meter is set to a high flow rate above 15 liters per minute. Therefore, with the present invention, the flow meter of the at least one source of medical gas can be safely adjusted from low flow rates to high flow rates, so that the fraction of an inspired medical gas, such as the fraction of inspired oxygen (FiO2), can be adjusted accordingly to accommodate the full range of a gas concentration for a patient's needs. For instance, the flow meter can be adjusted so that the present device can deliver a FiO2 within and beyond the range of 24% to 90%, with flow meter settings within and beyond 1 liter per minute to 40 liters per minute.

Third preferred embodiments may also allow access to the patient's mouth and nose through at least one of these at least one vent, aperture, cutaway, or gap of the mask. The light-weight and less cumbersome, open access feature of the preferred "open" face mask embodiment can prevent pressure build-up in the system and can allow for: the improved clearance of patient exhalation for nonrebreathing of carbon dioxide; better mixing of medical gas with ambient air; easier caregiver access to the patient's mouth, such as for suctioning, performing spirometry, incentive spirometry, peak flow, and other types of respiratory care and oral care; the ability for the patient to speak with less hindrance during treatment; the ability to drink through a straw during treatment; the reduced probability of aspiration; and the accommodation of a naso-gastric intubation tube for feeding and medicinal administration.

Along this medical gas tubing is at least one swivel element that is able to rotate freely to release twisting and tension on the medical gas tubing. Said swivel element can be located in the vicinity of the dampening disperser.

Figure 11:
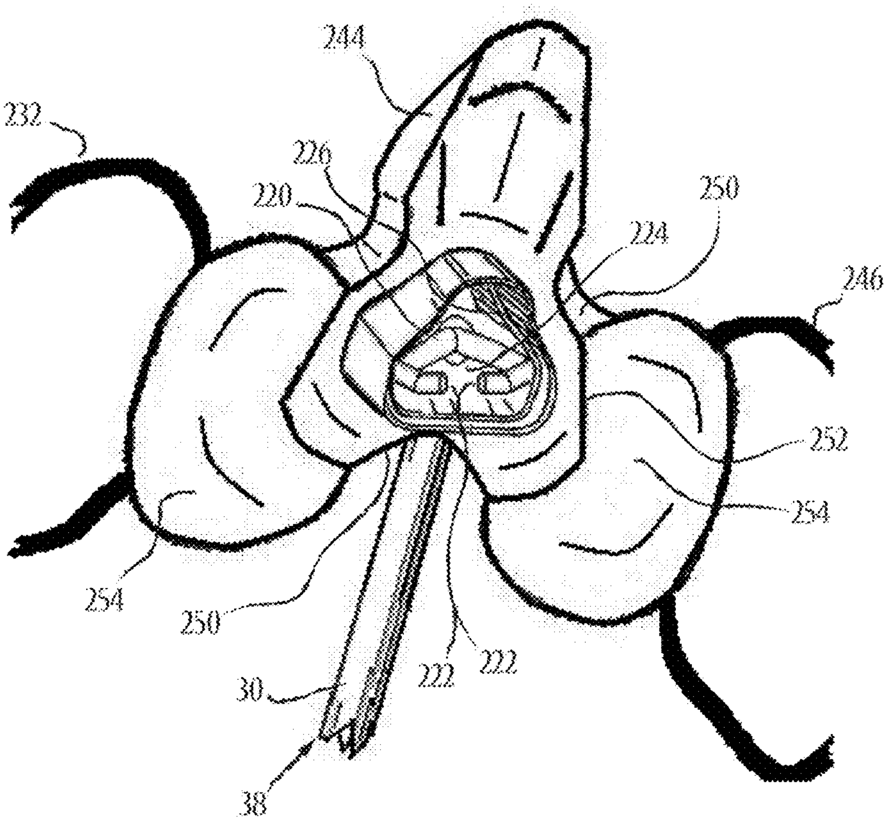
FIG. 11 is a detailed inner view of the dampening disperser and partial face mask housing of one of the third preferred embodiments of the universal medical gas delivery system. The disperser includes two gas outlet nozzles that release medical gas in somewhat counterposing directions to reduce gas velocity and to generate vortexing and mixing of gas with ambient air through gaps in the partial face mask housing. Elastic straps comprise the patient head interface in this figure. Cushioning elements and face mask rim are also shown.

In a third preferred embodiment FIG. 11, the medical gas delivery system 10 includes at least one dampening disperser 220 configured to be supported in a position in front of a patient's face. The dampening disperser 220 includes at least some concave walls 226 of an at least a partial face mask housing 244, and at least two gas outlets nozzles 222 that release medical gas within the interior region 224 formed by the concave interior walls 226 of the dampening disperser. The nozzles are in at least partially counterposing directions to disperse and reduce the velocity/impact of the gas flow 230 directed at the patient and coming from the at least one supply tubing 30 attached to an at least one medical gas source outlet 22 or 82. A turbulent plume of gases is generated that mix with ambient air in the space 228 in the vicinity of the patient's nose and mouth, such as between the upper lip and the base of the nose. In this manner both nose breathing and mouth breathing are allowed of these gases the clearance of exhaled breath away from the patient is aided so as to diminish the rebreathing of exhaled air. Said dampening disperser can be attached to a variety of different supports 232 in communication with the patient's head to position the dampening disperser in the vicinity of the patient's nose and mouth.

Figure 12:
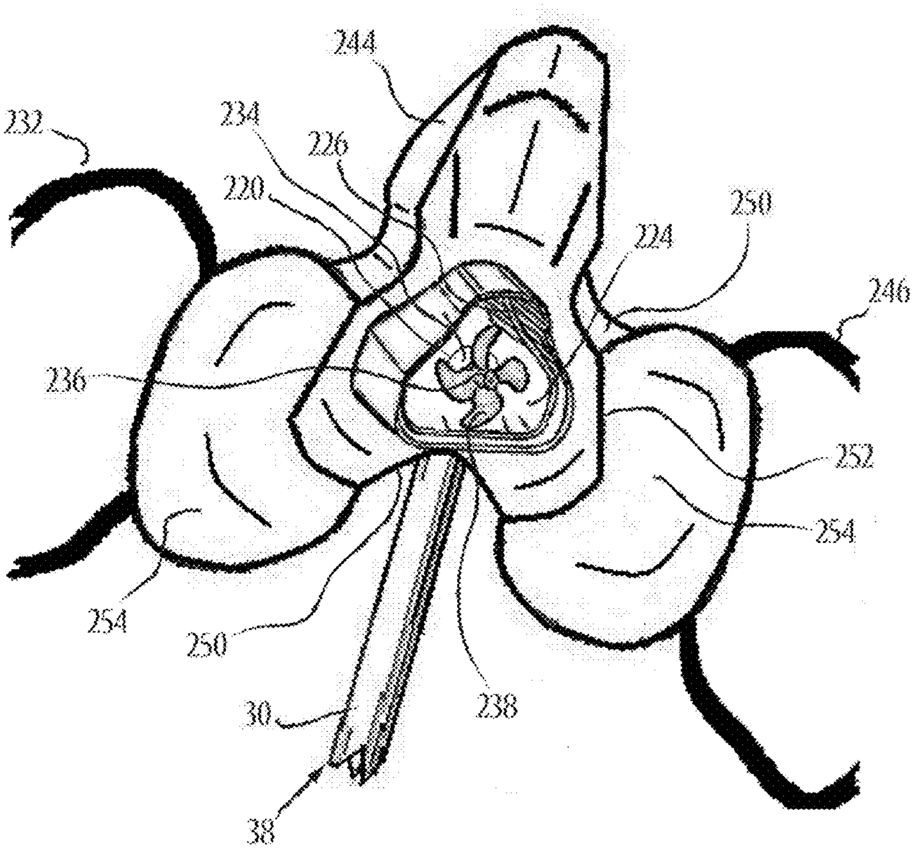
FIG. 12 is a detailed inner view of a partial face mask housing with an alternate dampening disperser, which includes a gas nozzle and a non-stationary baffle (impeller) that can reduce gas velocity and generate vortexing and mixing of gas with ambient air, as well as, to indicate air flow when in use.

In another third preferred embodiment FIG. 12, the least one dampening disperser 220 is configured to be supported in a position in front of a patient's face. The dampening disperser 220 includes at least some concave walls 226 of an at least a partial face mask housing 244, and at least one gas outlet nozzle 234 that releases medical gas within the interior region 224 formed by the concave interior walls 226 of the dampening disperser. At least one non-stationary baffle 236 is in the path of this gas flow to disperse and create drag. In this manner, the velocity/impact of the gas flow 230 is directed at the patient and is coming from the at least one supply tubing 30 attached to an at least one medical gas source outlet 22 or 82. This non-stationary baffle can also create cyclonic motion and vortices. A turbulent plume of gases is generated that mixes with ambient air in the space 228 in the vicinity of the patient's nose and mouth, such as between the upper lip and the base of the nose. Again, in this manner, both nose breathing and mouth breathing of these gases is allowed and the clearance of exhaled breath away from the patient is aided so as to diminish the rebreathing of exhaled air. Movement of said non-stationary baffle 236 may be visualized to indicate that the patient is receiving gas flow. The at least one gas outlet nozzle 234, and the at least one non-stationary baffle 236, may each be preferably positionable to adjust the delivery of the medical gas. The dampening disperser can be attached to a variety of different supports 232 in communication with the patient's head to position the dampening disperser in the vicinity of the patient's nose and mouth. Non-stationary baffles 236 can be chosen from a class of baffles selected from a type of non-stationary baffles including, but not limited to, flexible flaps, sails, parachutes, wings and blades and rotating blades 238, such as that of a fan, impeller, and windmill. The at least one non-stationary baffle 236 is preferably replaceable with a different non-stationary baffle from this class of non-stationary baffles to adjust the delivery of the medical gas.

Figure 13:
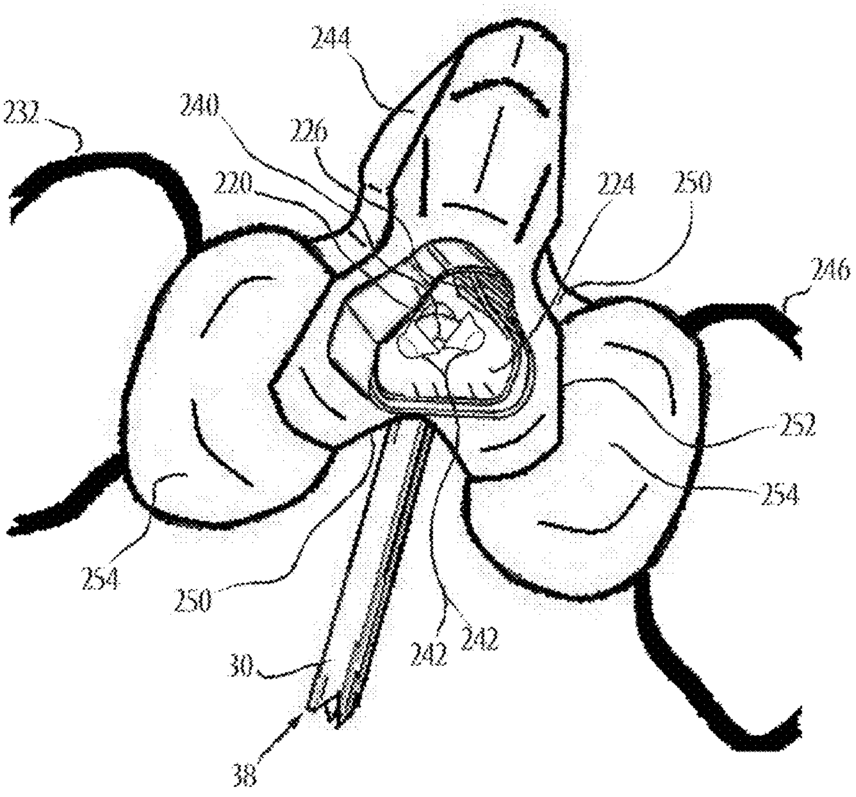
FIG. 13 is a detailed inner view of a partial face mask housing with an alternate dampening disperser, which includes two gas outlet nozzles positioned with two stationary (mushroom-like) baffles in its air flow trajectory, to reduce gas velocity and generate vortexing and mixing of gas with ambient air.

In another third preferred embodiment FIG. 13, the least one dampening disperser 220 is configured to be supported in a position in front of a patient's face. The dampening disperser 220 includes at least some concave walls 226 of an at least a partial face mask housing 244, and at least one gas outlet nozzle 240 that releases medical gas within the interior region 224 formed by the concave interior walls 226 of the dampening disperser. At least two baffles 242 are in the path of this gas flow to disperse and reduce the velocity/impact of the gas flow 230 directed at the patient and coming from the at least one supply tubing 30 attached to an at least one medical gas source outlet 22 or 82. A turbulent plume of gases is generated that mix with ambient air in the space 228 in the vicinity of the patient's nose and mouth, such as between the upper lip and the base of the nose. In this manner, both nose breathing and mouth breathing of these gases is allowed and the clearance of exhaled breath away from the patient is aided so as to diminish the rebreathing of exhaled air. The at least one gas outlet nozzle 240, and the at least two baffles 242, may each be preferably positionable to adjust the delivery of the medical gas. The at least two baffles 242 are also preferably replaceable with different baffles, baffles having different size and or shape, to adjust the delivery of said medical gas. The dampening disperser can be attached to a variety of different supports 232 in communication with the patient's head to position the dampening disperser in the vicinity of the patient's nose and mouth.

Figure 17:
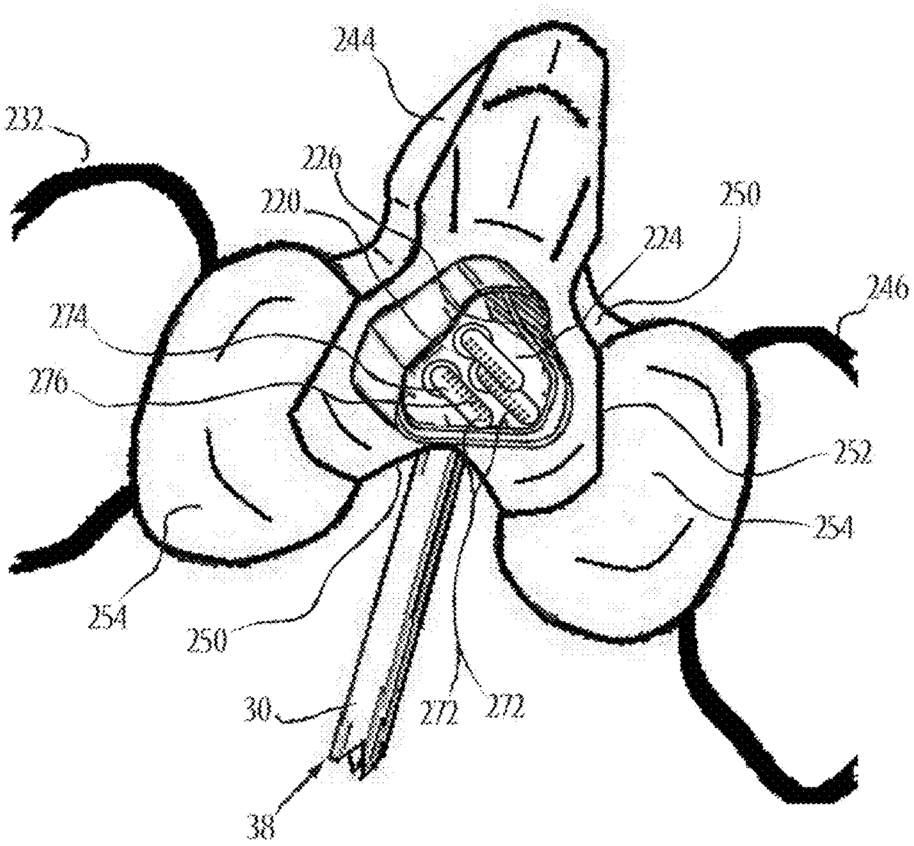
FIG. 17 is a detailed inner view of a partial face mask housing with an alternate dampening disperser, which includes at least one gas multi-outlet nozzle including an at least a partial tubular structure with a plurality of small/micro gas outlets to disperse and reduce a velocity of a gas flow and to generate vortexing and mixing of gas. This figure is shown with three gas multi-outlet nozzles, each having a straight tubular structure.
Figure 18:
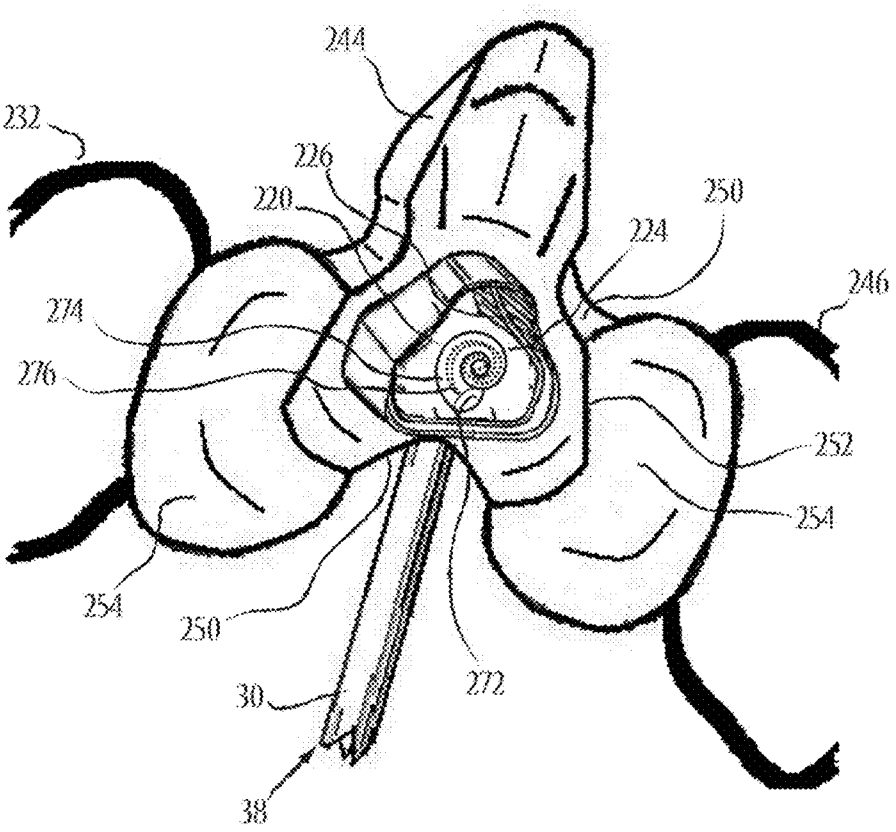
FIG. 18 is a detailed inner view of a partial face mask housing with this alternate dampening disperser, which includes at least one gas multi-outlet nozzle including an at least a partial tubular structure with a plurality of small/micro gas outlets to disperse and reduce a velocity of a gas flow and to generate vortexing and mixing of gas. This figure is shown with one gas multi-outlet nozzle having a curved/spiral tubular structure.

In another third preferred embodiment FIGS. 17 and 18, the least one dampening disperser 220 is configured to be supported in a position in front of a patient's face. The dampening disperser 220 includes at least some concave walls 226 of an at least a partial face mask housing 244, and at least one gas multi-outlet nozzle 272. The at least one gas multi-outlet nozzle 272 includes an at least a partial tubular structure 274 with a plurality of small/micro gas outlets 276 that release medical gas. The at least one gas multi-outlet nozzle 272 serves to disperse and reduce a velocity of a gas flow 230 coming from at least one medical gas supply tubing 30 attached to an at least one medical gas source outlet 22 or 82, while generating at least one plume of gases that mix with air in a space 228 in the vicinity of the patient's nose and mouth, chosen from vicinities including, but not limited to, between an upper lip and a base of the patient's nose, to allow for both nose breathing and mouth breathing of said at least one plume of gases and to aid in clearance of exhaled breath away from the patient so as to diminish rebreathing of exhaled air. FIG. 17 shows a dampening disperser 220 with three gas multi-outlet nozzles 272, each having a straight tubular structure 274; while FIG. 18 shows a dampening disperser 220 with one gas multi-outlet nozzle 272 having a curved/spiral tubular structure 274. In FIGS. 17 and 18, the at least one gas multi-outlet nozzle 272, which includes an at least a partial tubular structure 274 with a plurality of small/micro gas outlets 276, releases at least some medical gas in at least partially counterposing directions. The dampening disperser can be attached to a variety of different supports 232 in communication with the patient's head to position the dampening disperser in the vicinity of the patient's nose and mouth.

Figure 19:
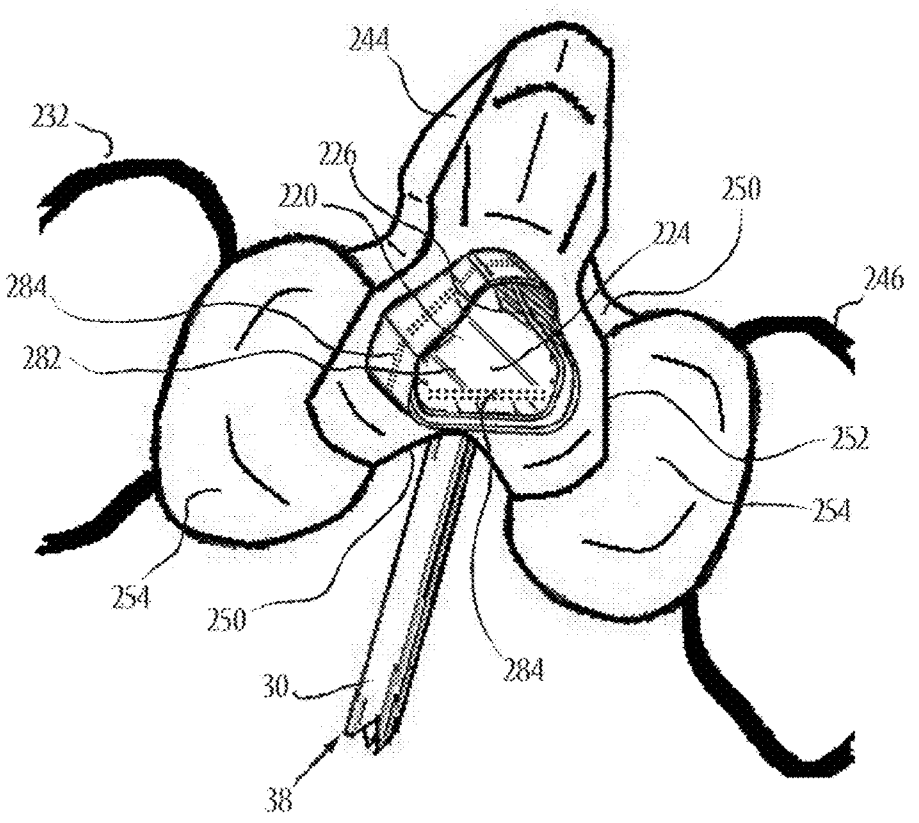
FIG. 19 is a detailed inner view of a partial face mask housing with an alternate dampening disperser, which includes channels/space within at least some concave walls of the partial face mask housing and adapted for a medical gas to pass. These at least some concave walls further include a plurality of small/micro gas outlets to disperse, refocus and reduce a velocity of a gas flow and to generate vortexing and mixing of gas.

In another third preferred embodiment FIG. 19, the least one dampening disperser 220 is configured to be supported in a position in front of a patient's face. The dampening disperser 220 includes at least some concave walls 226 of an at least a partial face mask housing 244. The at least some concave walls 226 of an at least a partial face mask housing 244 includes channels/space 282 within, which are adapted for a medical gas to pass. These at least some concave walls 226 of an at least a partial face mask housing 244 further include a plurality of small/micro gas outlets 284 on at least some portion of its surface that release medical gas in an interior region 224. The at least some concave walls 226 of an at least a partial face mask housing 244, which includes channels/space 282 within and a plurality of small/micro gas outlets 284, serve to disperse, refocus and reduce a velocity of a gas flow 230 coming from at least one medical gas supply tubing 30 attached to an at least one medical gas source outlet 22 or 82, while generating at least one plume of gases that mix with air in a space 228 in the vicinity of the patient's nose and mouth, chosen from vicinities including, but not limited to, between an upper lip and a base of the patient's nose, to allow for both nose breathing and mouth breathing of said at least one plume of gases and to aid in clearance of exhaled breath away from the patient so as to diminish rebreathing of exhaled air. The at least some concave walls 226 of an at least a partial face mask housing 244 with a plurality of small/micro gas outlets 284 release at least some medical gas in at least partially counterposing directions. The dampening disperser can be attached to a variety of different supports 232 in communication with the patient's head to position the dampening disperser in the vicinity of the patient's nose and mouth. In some embodiments, the at least some concave walls 226 preferably form an at least a partial prism-like shape.

Figure 14:
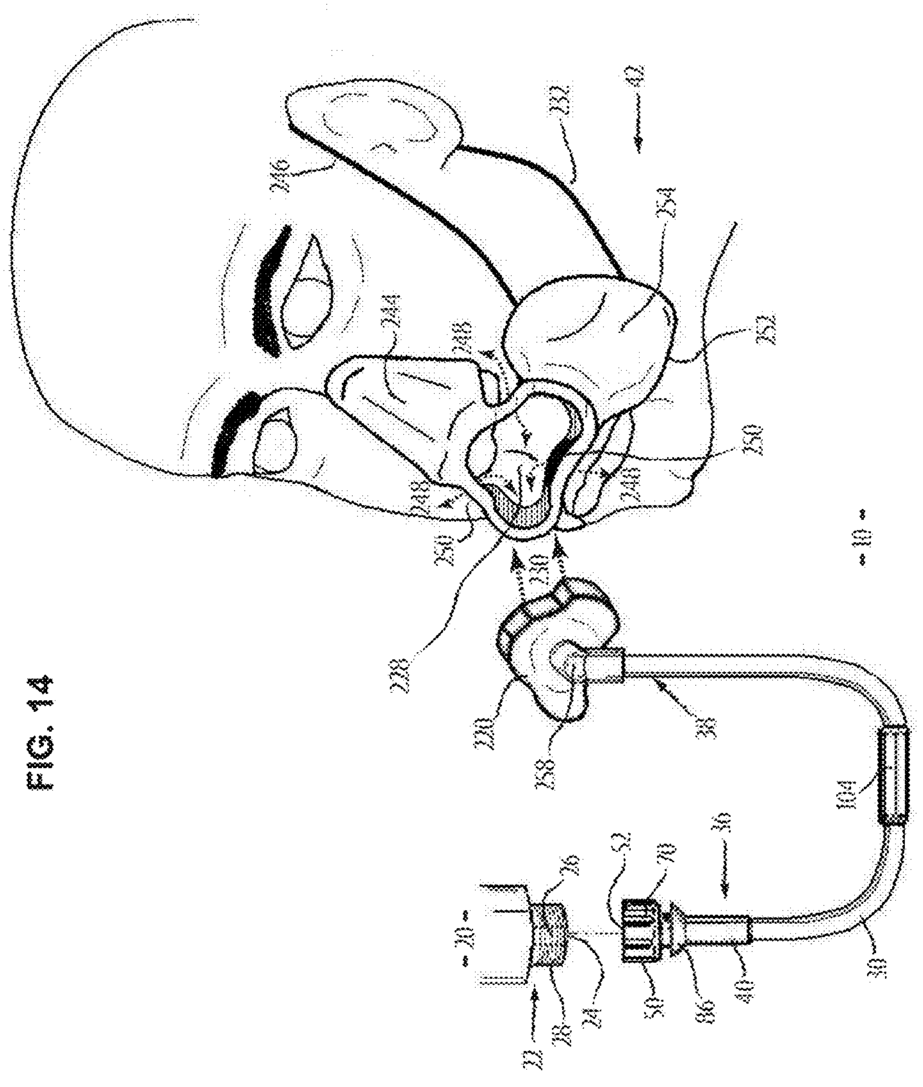
FIG. 14 is a side view of the universal medical gas delivery system of FIG. 1 with its dampening disperser detached from the partial face mask housing so as to show gas flowing from the dampening disperser to the patient, as well as, ambient air mixing in, and exhaled breath mixing out, of the space in the vicinity of the patient's nose and mouth. This figure also shows care giver access to the patient's nose and mouth through gaps/openings in this partial face mask housing. Cushioning elements and face mask rim are also shown.
Figure 15:
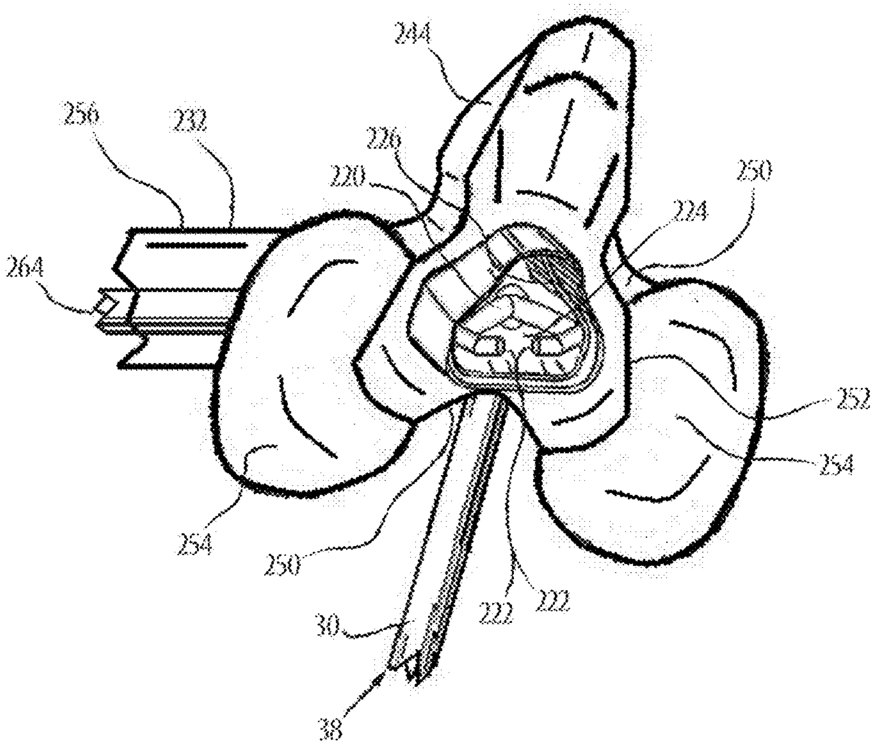
FIG. 15 is the partial face mask housing and dampening disperser as in FIG. 11, but with a boom that holds the dampening disperser in place, in the vicinity of the patient's nose and mouth, instead of straps. Not shown is that the support boom is further attached to head gear and/or neck gear as the patient interface. The boom can further support a gas sampling line that can connect to a monitoring device to determine the concentration of gases in the vicinity of the patient's nose and mouth, such as exhaled carbon dioxide.
Figure 16:
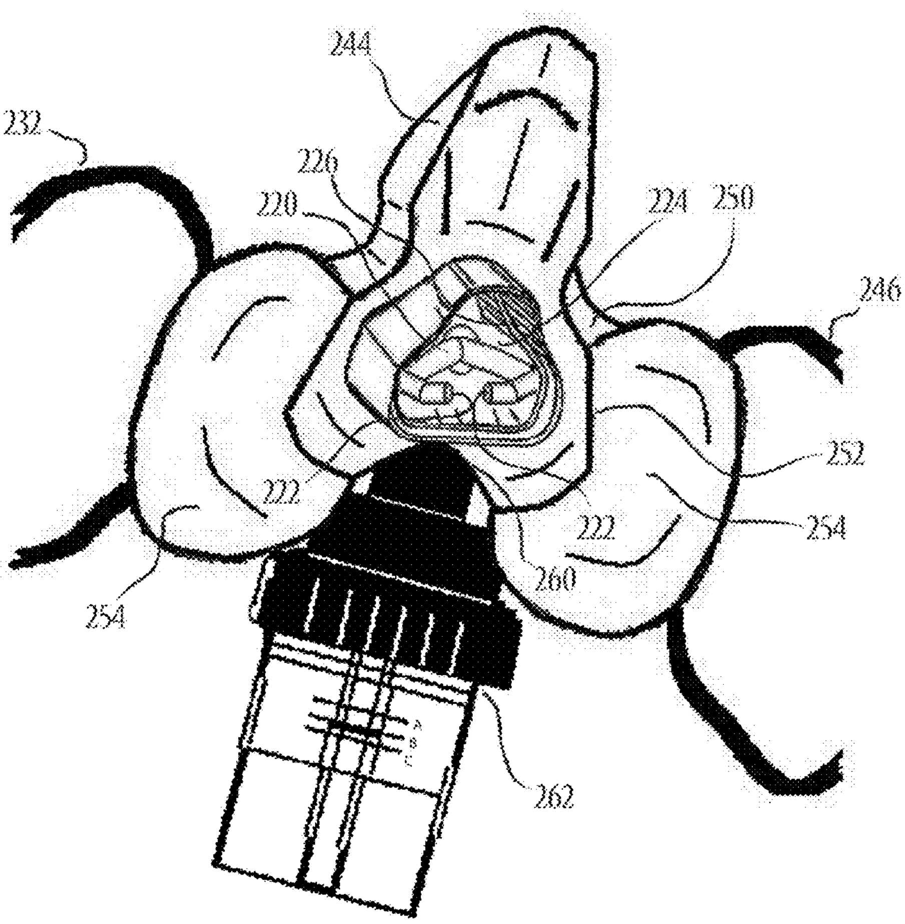
FIG. 16 is the partial face mask housing and dampening disperser as in FIG. 11, but further includes a nebulizer attached to an aerosol port for the administration of nebulizer treatments of medicament. The partial face mask housing directs the aerosol to a region in the vicinity of the patient's nose and mouth, without directing aerosol toward the patient's eyes.

In the third preferred embodiments, as shown in FIG. 14, the least one dampening disperser 220 is configured to be supported in a position in front of a patient's face. The dampening disperser 220 includes or serves as at least some concave walls 226 of an at least a partial face mask housing 244. The at least partial face mask housing 244 includes at least one fastener 246 to hold the face mask 244 in place on the patient's face. The face mask shown does not form an airtight seal between the mask and the patient's face. In this manner, at least some ambient air can enter and at least some dispensed gas and exhaled breath can exit. The space 228 is in the vicinity of the patient's nose and mouth. The movement of airflow 248 to and from the space in the vicinity of the patient's nose and mouth can be accomplished by at least one vent, aperture, cutaway, or gap 250 of the mask, which can prevent pressure build-up in the system. In preferred embodiments, this gap 250 can allow access to the patient's mouth and nose, such as for suctioning, performing spirometry, incentive spirometry, peak flow and other types of respiratory care and oral care. The patient is able to speak with less hindrance during treatment. The patient is able to drink through a straw during treatment. There is reduced probability of aspiration. A naso-gastric intubation tubing may be accommodated for feeding and medicinal administration. In this manner, the patient's feeling of claustrophobia is abated patient comfort is improved.

In these third alternate embodiments FIG. 14, the at least partial face mask housing 244 includes at least one fastener 246 to hold the face mask 244 in place on the patient's face. The face mask housing contains a rim 252 for at least some contact with the patient's face so as to support the positioning of the dampening disperser in the vicinity of the patient's nose and mouth. The rim is further preferably comprised of at least one cushioning element 254 for both patient comfort and also to elevate the dampening disperser at least some distance from the patient's face. The rim, or its cushioning, can be chosen from cushioning elements including, but not limited to, pads, thick elastomeric pads, fabric pads, gel containing pads, liquid containing pads, wax pads, wax-filled pads, silicone-filled pads, air-filled pads, balloons, air-filled skirts and any combination of one or more of these cushioning elements. Note that the air-filled skirts would utilize some of the gas dispensed from at least one gas outlet nozzle to fill the skirt to create a cushion of air which is ejected against the surface of the patient's face to create an "air cushion," similar to that which lifts a hovercraft. Inflation of this air cushion can indicate that medical gas is flowing through the system. The comfort pad may also be formable/adjustable to contour to the face and to help hold the mask in position. The streamlined face mask design reduces feelings of claustrophobia that patients often have with more cumbersome face masks.

In these third embodiments, at least one dampening disperser 220 is supported and held in position by an at least one support 232 chosen from a class of head associated supports selected from medical gas delivery supports including, but not limited to, fasteners, straps 246 (FIG. 11), bands, elastic bands, chin supports, glasses-like supports, over the ear supports, over the ear elastic bands, over the ear tubing supports, arms, booms 256 (FIG. 15) and elbow-like supports, etc and can include at least one swivel element 258, chosen from a class of swivel elements including, but not limited to, ball joints, hollow cylindrical rod-like housings that contain another rod-like structure of smaller diameter inside of it and allowed to rotate within it and cylindrical rod-like structures able to turn freely within a support structure, along with means of preventing said swivel element from dissociating, chosen from such means including, but not limited to nuts, washers, pins and flanges.

In these third alternate embodiments, the at least partial face mask housing 244 preferably includes at least one ambient air vent 250 chosen from a class of ambient air vents including, but not limited to, air vents that are non-adjustable, air vents that are adjustable, air vents that are filterable, air vents that are closeable, and air vents that are resealable.

Again, in these third alternate embodiments, the at least partial face mask housing 244 preferably includes an aerosol port 260 (FIG. 16) for attachment to a nebulizer 262. In this manner, the patient may also receive a nebulizer treatment while wearing the support of the dampening disperser. The airflow of the dampening disperser may direct aerosol flow to the nose and mouth of the patient and away from the patient's eyes, for a higher respirable dose of aerosol.

In these third alternate embodiments, the at least partial face mask housing 244 preferably includes a gas sampling tubing line 264 (FIG. 15) with inlet positioned in a space in the vicinity of the patient's nose and mouth and outlet connected to a gas monitoring device/sensor. The monitoring device monitors gas composition in this region, such as exhaled gases which may include determination of the carbon dioxide concentration and ratio of carbon dioxide to oxygen.

In these third alternate embodiments of the medical gas delivery system, the at least partial face mask housing 244 may also include a removable support adapter that can align the dampening disperser with an endotracheal tube for delivery of medical gas to an intubated patient.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention. Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A medical gas delivery system that includes at least one dampening disperser (220), configured to be supported in a position in front of a patient's face, said dampening disperser (220) including at least some concave walls (226) of an at least a partial face mask housing (244), at least one gas outlet nozzle (234) that releases medical gas, and at least one non-stationary baffle (236) in a path of gas flow (230) to disperse and create drag, thereby reducing a velocity of the gas flow (230) coming from at least one medical gas supply tubing (30) attached to an at least one medical gas source outlet (22 or 82), while generating a turbulent plume of gases that mix with air in a space (228) in a vicinity of a patient's nose and mouth, chosen from vicinities including, but not limited to, between an upper lip and a base of the patient's nose, to allow for both nose breathing and mouth breathing of said turbulent plume of gases and to aid in clearance of exhaled breath away from the patient so as to diminish rebreathing of exhaled air, movement of said non-stationary baffle (236) is visualized to indicate that the patient is receiving gas flow, said at least one non-stationary baffle (236) is chosen from a class of baffles selected from a type of non-stationary baffles including, but not limited to, flexible flaps, sails, parachutes, wings and blades and rotating blades (238), including rotating blades of a fan, impeller, and windmill.

2. A medical gas delivery system that includes at least one dampening disperser (220) as set forth in claim 1, whereby said at least one gas outlet nozzle (234) is positionable to adjust the delivery of said medical gas.

3. A medical gas delivery system that includes at least one dampening disperser (220) as set forth in claim 1, whereby said at least one non-stationary baffle (236) is positionable to adjust the delivery of said medical gas.

4. A medical gas delivery system that includes at least one dampening disperser (220) as set forth in claim 1, whereby said at least one non-stationary baffle (236) is replaceable with a different non-stationary baffle to adjust the delivery of said medical gas.

5. A medical gas delivery system that includes at least one dampening disperser (220) as set forth in claim 1, whereby said at least a partial face mask housing (244) includes at least one ambient air vent (250) chosen from a class of ambient air vents including, but not limited to, air vents that are non-adjustable, air vents that are adjustable, air vents that are filterable, air vents that are closeable, and air vents that are resealable.

6. A medical gas delivery system that includes at least one dampening disperser (220) as set forth in claim 1, whereby said at least a partial face mask housing (244) also includes an aerosol port (260), for attachment to a nebulizer (262), so that the patient receives a nebulizer treatment while wearing said at least a partial face mask housing (244).

7. A medical gas delivery system that includes at least one dampening disperser (220) as set forth in claim 1, whereby said at least a partial face mask housing (244) also includes a gas sampling tubing line (264), with inlet positioned in the space (228) in the vicinity of the patient's nose and mouth and outlet connected to a gas monitoring device/sensor, to monitor gas composition in the space (228) and to monitor exhaled gases, which includes determination of a carbon dioxide concentration and ratio of carbon dioxide to oxygen.

8. A medical gas delivery system that includes at least one dampening disperser (220) as set forth in claim 1, whereby said at least a partial face mask housing (244) also includes a removable support adapter that can align the dampening disperser with an endotracheal tube for delivery of medical gas to an intubated patient.

9. A medical gas delivery system that includes at least one dampening disperser (220), configured to be supported in a position in front of a patient's face, said dampening disperser (220) including at least some concave walls (226) of an at least a partial face mask housing (244), at least one gas outlet nozzle (240) that releases medical gas, and at least two baffles (242) in a path of gas flow (230) to disperse, refocus and reduce a velocity of the gas flow (230) coming from at least one medical gas supply tubing (30) attached to an at least one medical gas source outlet (22 or 82), while generating at least one turbulent plume of gases that mix with air in a space (228) in a vicinity of a patient's nose and mouth, chosen from vicinities including, but not limited to, between an upper lip and a base of the patient's nose, to allow for both nose breathing and mouth breathing of said turbulent plume of gases and to aid in clearance of exhaled breath away from the patient so as to diminish rebreathing of exhaled air.

10. A medical gas delivery system that includes at least one dampening disperser (220) as set forth in claim 9, whereby said at least one gas outlet nozzle (240) is positionable to adjust the delivery of said medical gas.

11. A medical gas delivery system that includes at least one dampening disperser (220) as set forth in claim 9, whereby said at least two baffles (242) are positionable to adjust the delivery of said medical gas.

12. A medical gas delivery system that includes at least one dampening disperser (220) as set forth in claim 9, whereby said at least two baffles (242) are replaceable with different baffles, baffles having different size and or shape, to adjust the delivery of said medical gas.

13. A medical gas delivery system that includes at least one dampening disperser (220) as set forth in claim 9, whereby said at least a partial face mask housing (244) includes at least one ambient air vent (250) chosen from a class of ambient air vents including, but not limited to, air vents that are non-adjustable, air vents that are adjustable, air vents that are filterable, air vents that are closeable, and air vents that are resealable.

14. A medical gas delivery system that includes at least one dampening disperser (220) as set forth in claim 9, whereby said at least a partial face mask housing (244) also includes an aerosol port (260), for attachment to a nebulizer (262), so that the patient receives a nebulizer treatment while wearing said at least a partial face mask housing (244).

15. A medical gas delivery system that includes at least one dampening disperser (220) as set forth in claim 9, whereby said at least a partial face mask housing (244) also includes a gas sampling tubing line (264), with inlet positioned in the space (228) in the vicinity of the patient's nose and mouth and outlet connected to a gas monitoring device/sensor, to monitor gas composition in the space (228) and to monitor exhaled gases, which includes determination of a carbon dioxide concentration and ratio of carbon dioxide to oxygen.

16. A medical gas delivery system that includes at least one dampening disperser (220) as set forth in claim 9, whereby said at least a partial face mask housing (244) also includes a removable support adapter that can align the dampening disperser with an endotracheal tube for delivery of medical gas to an intubated patient.

17. A medical gas delivery system that includes at least one dampening disperser (220); configured to be supported in a position in front of a patient's face, said dampening disperser (220) including at least some concave walls (226) of an at least a partial face mask housing (244), and at least one gas multi-outlet nozzle (272), said at least one gas multi-outlet nozzle (272) including an at least a partial tubular structure (274) with a plurality of small/micro gas outlets (276) that release medical gas, said at least one gas multi-outlet nozzle (272) serving to disperse and reduce a velocity of a gas flow (230) coming from at least one medical gas supply tubing (30) attached to an at least one medical gas source outlet (22 or 82), while generating at least one plume of gases that mix with air in a space (228) in a vicinity of the patient's nose and mouth, chosen from vicinities including, but not limited to, between an upper lip and a base of the patient's nose, to allow for both nose breathing and mouth breathing of said at least one plume of gases and to aid in clearance of exhaled breath away from the patient so as to diminish rebreathing of exhaled air.

18. A medical gas delivery system that includes at least one dampening disperser (220) as set forth in claim 17, whereby said at least a partial tubular structure (274) is straight.

19. A medical gas delivery system that includes at least one dampening disperser (220) as set forth in claim 17, whereby said at least a partial tubular structure (274) includes at least some curved portions.

20. A medical gas delivery system that includes at least one dampening disperser (220) as set forth in claim 17, whereby said at least one gas multi-outlet nozzle (272) including an at least a partial tubular structure (274) with a plurality of small/micro gas outlets (276) releases at least some medical gas in at least partially counterposing directions.

21. A medical gas delivery system that includes at least one dampening disperser (220) as set forth in claim 17, whereby said at least a partial face mask housing (244) includes at least one ambient air vent (250) chosen from a class of ambient air vents including, but not limited to, air vents that are non-adjustable, air vents that are adjustable, air vents that are filterable, air vents that are closeable, and air vents that are resealable.

22. A medical gas delivery system that includes at least one dampening disperser (220) as set forth in claim 17, whereby said at least a partial face mask housing (244) also includes an aerosol port (260), for attachment to a nebulizer (262), so that the patient receives a nebulizer treatment while wearing said at least a partial face mask housing (244).

23. A medical gas delivery system that includes at least one dampening disperser (220) as set forth in claim 17, whereby said at least a partial face mask housing (244) also includes a gas sampling tubing line (264), with inlet positioned in the space (228) in the vicinity of the patient's nose and mouth and outlet connected to a gas monitoring device/sensor, to monitor gas composition in the space (228) and to monitor exhaled gases, which includes determination of a carbon dioxide concentration and ratio of carbon dioxide to oxygen.

24. A medical gas delivery system that includes at least one dampening disperser (220) as set forth in claim 17, whereby said at least a partial face mask housing (244) also includes a removable support adapter that can align the dampening disperser with an endotracheal tube for delivery of medical gas to an intubated patient.

25. A medical gas delivery system that includes at least one dampening disperser (220); configured to be supported in a position in front of a patient's face, said dampening disperser (220) including at least some concave walls (226) of an at least a partial face mask housing (244), said at least some concave walls (226) of said at least a partial face mask housing (244) including channels/space (282) within said at least some concave walls (226) and adapted for a medical gas to pass, said at least some concave walls (226) of said at least a partial face mask housing (244) further including a plurality of small/micro gas outlets (284) on at least some portion of a surface that release said medical gas, said at least some concave walls (226) of said at least a partial face mask housing (244) including said channels/space (282) within and including said plurality of small/micro gas outlets (284) serving to disperse, refocus and reduce a velocity of a gas flow (230) coming from at least one medical gas supply tubing (30) attached to an at least one medical gas source outlet (22 or 82), while generating at least one plume of gases that mix with air in a space (228) in a vicinity of the patient's nose and mouth, chosen from vicinities including, but not limited to, between an upper lip and a base of the patient's nose, to allow for both nose breathing and mouth breathing of said at least one plume of gases and to aid in clearance of exhaled breath away from the patient so as to diminish rebreathing of exhaled air.

26. A medical gas delivery system that includes at least one dampening disperser (220) as set forth in claim 25, whereby said at least some concave walls (226) forms an at least a partial prism-like shape.

27. A medical gas delivery system that includes at least one dampening disperser (220) as set forth in claim 25, whereby said at least some concave walls (226) of said at least a partial face mask housing (244) with a plurality of small/micro gas outlets (284) release at least some medical gas in at least partially counterposing directions.

28. A medical gas delivery system that includes at least one dampening disperser (220) as set forth in claim 25, whereby said at least a partial face mask housing (244) includes at least one ambient air vent (250) chosen from a class of ambient air vents including, but not limited to, air vents that are non-adjustable, air vents that are adjustable, air vents that are filterable, air vents that are closeable, and air vents that are resealable.

29. A medical gas delivery system that includes at least one dampening disperser (220) as set forth in claim 25, whereby said at least a partial face mask housing (244) also includes an aerosol port (260), for attachment to a nebulizer (262), so that the patient receives a nebulizer treatment while wearing said at least a partial face mask housing (244).

30. A medical gas delivery system that includes at least one dampening disperser (220) as set forth in claim 25, whereby said at least a partial face mask housing (244) also includes a gas sampling tubing line (264), with inlet positioned in the space (228) in the vicinity of the patient's nose and mouth and outlet connected to a gas monitoring device/sensor, to monitor gas composition in the space (228) and to monitor exhaled gases, which includes determination of a carbon dioxide concentration and ratio of carbon dioxide to oxygen.

31. A medical gas delivery system that includes at least one dampening disperser (220) as set forth in claim 25, whereby said at least a partial face mask housing (244) also includes a removable support adapter that can align the dampening disperser with an endotracheal tube for delivery of medical gas to an intubated patient.

* * * * *